United States Patent
Ruben et al.

(10) Patent No.: US 12,233,477 B2
(45) Date of Patent: *Feb. 25, 2025

(54) HERMETIC ASSEMBLY AND DEVICE INCLUDING SAME

(71) Applicant: MEDTRONIC, INC., Minneapolis, MN (US)

(72) Inventors: David A. Ruben, Mesa, AZ (US); Andreas Fenner, Chandler, AZ (US); Andrew J. Ries, Lino Lakes, MN (US); Robert A Munoz, Andover, MN (US); Christopher T. Kinsey, Bethel, MN (US); Mark E. Henschel, Phoenix, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/404,992

(22) Filed: Jan. 5, 2024

(65) Prior Publication Data

US 2024/0131625 A1 Apr. 25, 2024

Related U.S. Application Data

(63) Continuation of application No. 17/118,283, filed on Dec. 10, 2020, now Pat. No. 11,865,639.

(60) Provisional application No. 62/947,924, filed on Dec. 13, 2019.

(51) Int. Cl.
*B23K 26/20* (2014.01)
*A61N 1/375* (2006.01)
*A61N 1/39* (2006.01)
*B23K 26/32* (2014.01)

(52) U.S. Cl.
CPC .......... *B23K 26/206* (2013.01); *A61N 1/3754* (2013.01); *A61N 1/3968* (2013.01); *B23K 26/32* (2013.01)

(58) Field of Classification Search
None
See application file for complete search history.

(56) References Cited

U.S. PATENT DOCUMENTS

| | | | |
|---|---|---|---|
| 5,333,095 A | 7/1994 | Stevenson | |
| 5,905,627 A * | 5/1999 | Brendel | H01G 4/35 |
| 5,999,398 A | 12/1999 | Makl | |
| 6,414,835 B1 * | 7/2002 | Wolf | A61N 1/3754 |
| | | | 361/306.3 |

(Continued)

OTHER PUBLICATIONS

International Search Report and Written Opinion from PCT/US2020/064445 dated Mar. 16, 2021 (10 pages).

*Primary Examiner* — Krystal Robinson
(74) *Attorney, Agent, or Firm* — Mueting Raasch Group

(57) ABSTRACT

Various embodiments of a hermetic assembly and a method of forming such assembly are disclosed. The hermetic assembly includes a dielectric substrate having a first major surface and a second major surface, a patterned layer connected to the first major surface of the dielectric substrate by a laser bond, and a ferrule having a body and a flange extending from the body. The flange is welded to a welding portion of the patterned layer that is disposed between the flange and the first major surface of the dielectric substrate such that the ferrule is hermetically sealed to the dielectric substrate.

20 Claims, 11 Drawing Sheets

(56) References Cited

U.S. PATENT DOCUMENTS

| | | | |
|---|---|---|---|
| 6,778,040 B2* | 8/2004 | Kim | H05K 9/0066 |
| | | | 333/182 |
| 10,124,559 B2 | 11/2018 | Sandlin et al. | |
| 2010/0280584 A1* | 11/2010 | Johnson | A61N 1/05 |
| | | | 607/116 |
| 2011/0317965 A1 | 12/2011 | Fijimura | |
| 2013/0035733 A1 | 2/2013 | Breyen | |
| 2013/0127567 A1 | 5/2013 | Iyer | |
| 2014/0049924 A1* | 2/2014 | Deininger | H01R 43/26 |
| | | | 361/752 |
| 2014/0254983 A1* | 9/2014 | Moriya | G02B 6/4251 |
| | | | 228/175 |
| 2014/0262493 A1* | 9/2014 | Markham | B23K 26/20 |
| | | | 174/650 |
| 2015/0314131 A1 | 11/2015 | Stevenson | |
| 2015/0321016 A1* | 11/2015 | O'Brien | A61N 1/37217 |
| | | | 607/62 |
| 2016/0184593 A1 | 6/2016 | Ruben | |
| 2017/0172505 A1* | 6/2017 | Ruben | H05K 5/069 |
| 2018/0263132 A1 | 9/2018 | Ruben | |
| 2018/0279924 A1 | 10/2018 | Kuhn | |
| 2019/0166709 A1 | 5/2019 | Ruben | |
| 2019/0290920 A1 | 9/2019 | Stevenson | |
| 2020/0368537 A1* | 11/2020 | Nidelkoff | H05K 5/0091 |

\* cited by examiner

HERMETIC ASSEMBLY AND DEVICE INCLUDING SAME

CROSS-REFERENCE TO RELATED APPLICATIONS

This application is a continuation of U.S. patent application Ser. No. 17/118,283, filed Dec. 10, 2020, and which claims the benefit of U.S. Provisional Application No. 62/947,924, filed Dec. 13, 2019, the disclosure of which are incorporated by reference herein in their entireties.

TECHNICAL FIELD

This disclosure generally relates to hermetic assemblies that include a ferrule and devices that include such assemblies.

BACKGROUND

Various systems require a hermetic seal between a window and a housing. Oftentimes, the window may include dielectric materials while the housing may include metallic metals. Such devices may include a sensor or port that requires that the window be transmissive to electromagnetic radiation for emission or detection or for viewing one or more components that are disposed within the housing.

Further, other systems may require electrical coupling between electrical devices disposed within a hermetically sealed enclosure and external devices. Oftentimes, such electrical coupling needs to withstand various environmental factors such that a conductive pathway or pathways from the external surface to within the enclosure remains stable. For example, implantable medical devices (IMDs), e.g., cardiac pacemakers, defibrillators, neurostimulators, and drug pumps, which include electronic circuitry and battery elements, require an enclosure or housing to contain and hermetically seal these elements within a body of a patient. Many of these IMDs include one or more electrical feedthrough assemblies to provide electrical connections between the elements contained within the housing and components of the IMD external to the housing, for example, sensors and/or electrodes and/or lead wires mounted on an exterior surface of the housing, or electrical contacts housed within a connector header, which is mounted on the housing to provide coupling for one or more implantable leads. Such leads typically carry one or more electrodes and/or one or more other types of physiological sensors.

A feedthrough assembly typically includes one or more feedthrough pins that extend between an interior and an exterior of the housing through a ferrule. Each feedthrough pin is electrically isolated from the ferrule, and, for multipolar assemblies, from one another, by an insulator element, e.g., glass or ceramic, that is mounted within the ferrule and surrounds the feedthrough pin(s). Glass insulators are typically sealed directly to the pin(s) and to the ferrule, e.g., by heating the assembly to a temperature at which the glass wets the pin(s) and ferrule, while ceramic insulators are typically sealed to the pin(s) and to the ferrule by a braze joint. High temperatures are typically required to join corrosion-resistant conductive materials with corrosion-resistant insulative materials.

SUMMARY

The techniques of this disclosure generally relate to various embodiments of a hermetic assembly. The assembly includes a ferrule that includes a body and a flange that extends from the body. The flange is welded to a welding portion of a patterned layer disposed between the flange and a first major surface of a dielectric substrate of the assembly such that the ferrule is hermetically sealed to the dielectric substrate. The hermetic assembly can form a part of a hermetically-sealed package, where a housing of the package can be connected to the ferrule of the assembly.

In one example, aspects of this disclosure relate to a hermetic assembly that includes a dielectric substrate having a first major surface and a second major surface, a patterned layer connected to the first major surface of the dielectric substrate by a laser bond, and a ferrule having a body and a flange extending from the body. The flange is welded to a welding portion of the patterned layer that is disposed between the flange and the first major surface of the dielectric substrate such that the ferrule is hermetically sealed to the dielectric substrate.

In another example, aspects of this disclosure relate to a hermetically-sealed package that includes a housing and a hermetic assembly that forms a part of the housing. The hermetic assembly includes a dielectric substrate having a first major surface and a second major surface, a patterned layer connected to the first major surface of the dielectric substrate by a laser bond, and a ferrule having a body and a flange extending from the body. The flange is welded to a welding portion of the patterned layer that is disposed between the flange and the first major surface of the dielectric substrate such that the ferrule is hermetically sealed to the dielectric substrate. An edge of the body of the ferrule is connected to an edge of the housing.

In another example, aspects of this disclosure related to a method that includes laser bonding a patterned layer to a first major surface of a dielectric substrate, and welding a flange of a ferrule to a welding portion of the patterned layer such that the welding portion is between the flange and the first major surface of the dielectric substrate and the ferrule is hermetically sealed to the dielectric substrate. The flange extends from a body of the ferrule.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
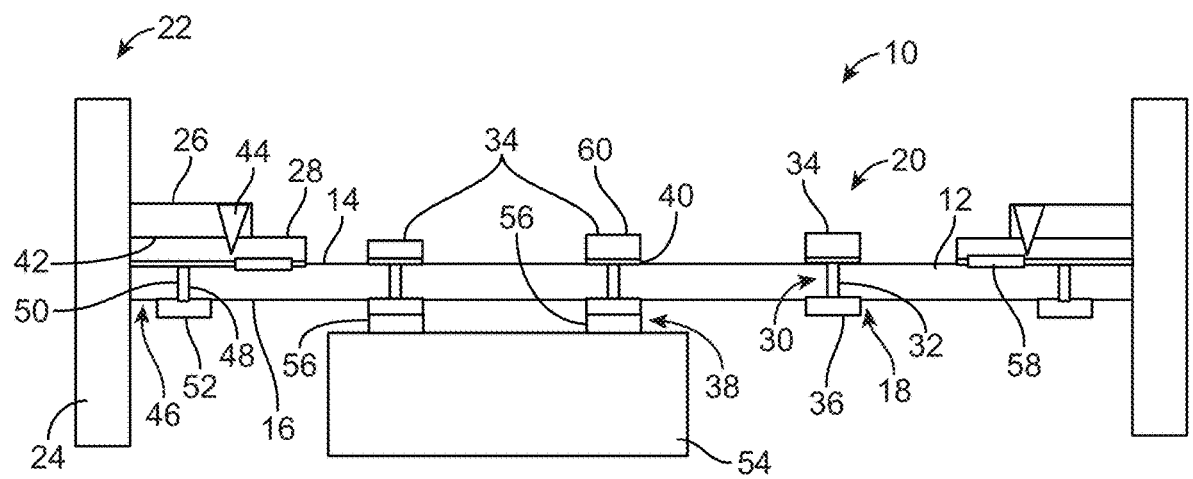
FIG. 1 is a schematic cross-section view of one embodiment of a hermetic assembly.

The techniques of this disclosure generally relate to various embodiments of a hermetic assembly. The assembly includes a ferrule that includes a body and a flange that extends from the body. As used herein, the term "ferrule" refers to an element or component that resides between two or more additional components to facilitate physical connection and/or provides structural support of the components in the assembly. The flange is welded to a welding portion of a patterned layer disposed between the flange and a first major surface of a dielectric substrate of the assembly such that the ferrule is hermetically sealed to the dielectric substrate. The hermetic assembly can form a part of a hermetically-sealed package, where a housing of the package can be connected to the ferrule of the assembly.

Some feedthrough assemblies include a dielectric substrate that is connected to a metal battery or housing. Bonding of a dielectric material to a metal material can, however, be challenging. Some techniques for performing such bonding require a bonding surface of the metal battery or housing be polished such that it is extremely smooth. Such smooth bonding surfaces have to be kept clean prior to bonding so that flat, smooth, clean surfaces are presented for bonding.

Other techniques for bonding dielectric and metal materials include bonding or brazing a weld ring to a dielectric wafer and then welding the metal housing or battery to the weld ring. These techniques, however, can still require that bonding surfaces of the dielectric wafer and the weld ring be polished such that they are extremely smooth. And while a brazed weld ring may not require the same level of surface preparation as is required for other types of bonding, brazing is a high-temperature process that can create stress in the materials and limit the process order as well as size, shape, and design of the assembly due to such thermal stresses.

One or more embodiments of the present disclosure provide a hermetic assembly that includes a ferrule having a flange that is welded to a patterned layer disposed on a major surface of a dielectric substrate. The ferrule can be connected to a housing or battery with minimal or no polishing or use of a weld ring. Further, the ferrule can allow for thinner housing sidewalls and provides more area on the dielectric substrate for electronic components as compared to assemblies that utilize weld rings or other attachment techniques. One or more embodiments of the present disclosure can further simplify attachment of a housing to the dielectric substrate of the hermetic assembly. Further, the ferrule can aid in protecting edges of the dielectric substrate and also isolate the substrate from some external loads that can damage the substrate. One or more embodiments of ferrules described herein may be bonded only to one side of the dielectric substrate without needing to be bonded to the other side of such substrate. Further, bonding of the ferrule to the substrate after components have been disposed on the substrate is possible as high process temperatures typically needed for brazing ferrules to substrates are not necessary.

The various embodiments of hermetic assemblies described herein can be included in hermetically-sealed packages that can be utilized for any suitable application. In one or more embodiments, the hermetically-sealed package can maintain the integrity of a conductive pathway that connects an external contact electrode or device to components disposed within the package while protecting enclosed electronic devices or circuitry from undesired external environmental factors.

The various embodiments of hermetic assemblies and hermetically-sealed packages that include such assemblies can be utilized with any suitable devices or systems, e.g., electronic systems used, e.g., in smartphones, tablets, laptop computers, construction equipment, underwater equipment, implantable medical devices, etc.

Figure 2:
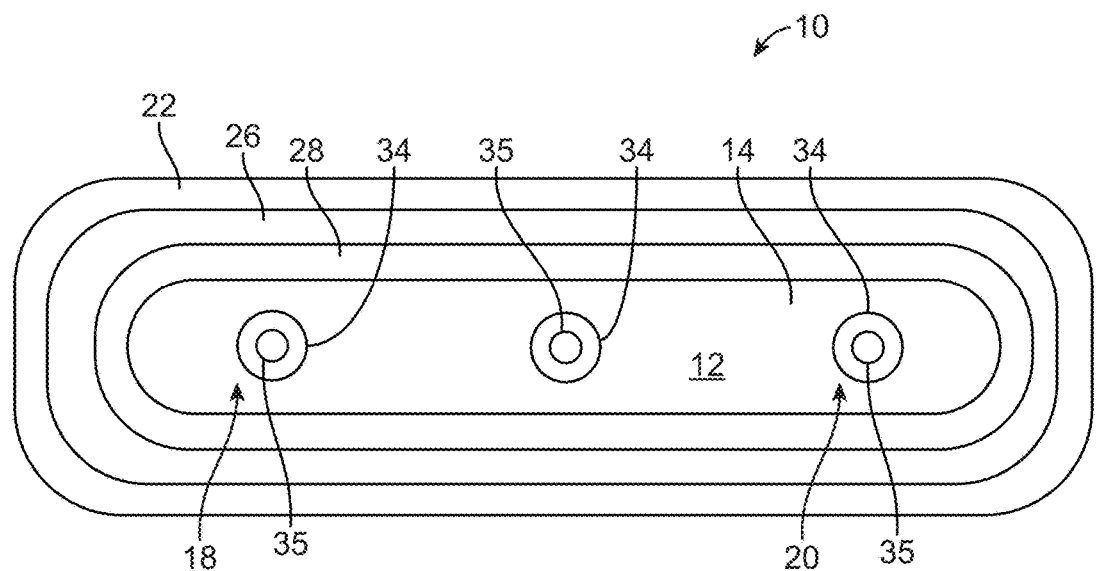
FIG. 2 is a schematic top plan view of the hermetic assembly of FIG. 1.

FIGS. 1-2 are various schematic views of one embodiment of a hermetic assembly 10. In one or more embodiments, the hermetic assembly 10 can be a feedthrough assembly as it includes one or more feedthroughs 18 as is further described herein. The assembly 10 includes a dielectric substrate 12 having a first major surface 14 and a second major surface 16, a feedthrough 18 disposed in the dielectric substrate, and a patterned layer 20 connected to the first major surface of the dielectric substrate. In one or more embodiments, the patterned layer 20 can be a patterned conductive layer. The assembly 10 further includes a ferrule 22 that has a body 24 and a flange 26 extending from the body. The ferrule 22 is connected to a welding portion 28 of the patterned conductive layer 20 that is disposed between the flange 26 and the first major surface 14 of the dielectric substrate 12 such that the ferrule is hermetically sealed to the dielectric substrate.

The dielectric substrate 12 can include any suitable material or materials. In one or more embodiments, the substrate 12 can include a dielectric material, e.g., at least one of glass, quartz, silica, sapphire, silicon carbide, diamond, or gallium nitride. Further, the substrate 12 can include at least one of a biocompatible material or one or more coatings or layers that can provide biocompatibility.

In one or more embodiments, the substrate 12 can be a transparent substrate. As used herein, the phrase "transparent substrate" refers to a substrate that can transmit a given percentage of electromagnetic radiation incident thereon during use of laser bonding techniques described herein to preferentially heat only a major surface of the substrate (e.g., first major surface 14 or second major surface 16 of substrate 12), and not an inner bulk of the substrate, thereby creating a bond that has a relatively greater strength than the bulk strength of the substrate. In one or more embodiments, the substrate 12 can be substantially transparent at a desired wavelength or range of wavelengths. As used herein, the phrase "substantially transparent" means that the substrate transmits greater than 50% of electromagnetic radiation incident on the substrate for a selected wavelength or range of wavelengths, assuming no reflection at the air-substrate boundaries. In one or more embodiments, the substrate 12 can be substantially transmissive to electromagnetic radiation having a wavelength of at least 200 nm. In one or more embodiments, the substrate 12 can be substantially transmissive to electromagnetic radiation having a wavelength of greater than 10,000 nm. In one or more embodiments, the substrate 12 can be substantially transmissive to electromagnetic radiation having a wavelength in a range of 200 nm to 10,000 nm. In one or more embodiments, the substrate 12 can be substantially transmissive to at least one of UV light, visible light, or IR light.

The substrate 12 can include any suitable dimensions, e.g., thicknesses. Further, the substrate 12 can take any suitable shape or shapes. The substrate 12 can be a single, unitary substrate or multiple substrates joined together using any suitable technique or techniques.

Disposed in the substrate 12 is the feedthrough 18, which can include any suitable feedthrough or feedthroughs that provide an electrical connection between the first major surface 14 and the second major surface 16 of the substrate. In one or more embodiments, the assembly 10 can include an array of feedthroughs 18. The hermetic assembly 10 can include any suitable number of feedthroughs, e.g., 1, 2, 3, 4, 5, 10, 20, or more feedthroughs. Each feedthrough 18 of the assembly 10 can be substantially identical in construction. In one or more embodiments, one or more feedthroughs can have characteristics that are different from one or more additional feedthroughs. The feedthrough 18 can include a via 30 disposed between the first major surface 14 and the second surface 16 of the substrate 12. A conductive material 32 can be disposed in the via 30 to provide an electrical pathway between the first major surface 14 and the second major surface 16 of the substrate 12.

The feedthrough 18 can also include an external contact 34. In one or more embodiments, the external contact 34 can be a portion of the patterned conductive layer 20 that is disposed adjacent the first major surface 14 of the substrate 12. As used herein, the term "adjacent the first major surface of the substrate" means that an element or component is disposed closer to the first major surface of the substrate than to the second major surface of the substrate. In one or more embodiments, the external contact 34 can be disposed on the first major surface 14 of the substrate 12. The external contact 34 can be disposed over the via 30 adjacent the first major surface 14 of the substrate 12. In one or more embodiments, the external contact 34 can be electrically connected to the conductive material 32 disposed in the via 30. The external contact 34 can be hermetically sealed to the first major surface 14 of the substrate 12 using any suitable technique or techniques.

The via 30 of the feedthrough 18 can be any suitable dimensions and take any suitable shape. The size and shape of the via 30 is predicated on the thickness of the substrate 12 and the techniques utilized to provide the conductive material 32 that forms the electrical pathway between the first major surface 14 and the second major surface 16 of the substrate 12. Exemplary shapes for the via 30 can include parallel surface walls and/or tapered surface walls. In one or more embodiments where the substrate 12 has a thickness of approximately 100 to 500 µm, a typical opening for the via 30 at the first major surface 14 of the substrate 12 can be no greater than 500 µm, or no greater than 250 µm, or no greater than 100 micrometers, or no greater than 80 micrometers, or no greater than 50 micrometers, or no greater than 10 micrometers. Of course, the diameter of the via 30 could be larger (or smaller) than the illustrated examples based on the substrate thickness and/or the techniques utilized to provide the conductive material that forms the electrical pathway. Any suitable technique or techniques can be utilized to form the via 30, e.g., drilling, chemical etching, laser etching, etc.

The feedthrough 18 can also include the conductive material 32 disposed in the via 30 to provide a conductive pathway between the first major surface 14 and the second major surface 16 of substrate 12. The conductive material 32 can include any suitable conductive material or conductive materials, e.g., copper, titanium, aluminum, chromium, nickel, gold, platinum, composites (e.g., silver-filled epoxies), and combinations thereof. The conductive material 32 can be disposed in the via 30 using any suitable technique or techniques to provide a conductive pathway from external contact 34 to one or more devices or contacts disposed on or adjacent the second major surface 16 of the substrate 12. In one or more embodiments, the conductive material 32 can be disposed in the via 30 such that it substantially fills the via. In one or more embodiments, the conductive material 32 can be disposed in the via along sidewalls of the via and the opening of the via at the first major surface 14.

The feedthrough 18 can also include the external contact 34. In one or more embodiments, the external contact 34 can be adapted to electrically couple the feedthrough 18 to a conductor or a contact of a device, e.g., a contact of a header of an implantable medical device. Such conductors and contacts can be electrically coupled to the external contact 34 using any suitable technique or techniques, e.g., soldering, physical contact, welding, etc. The external contact 34 can include any suitable conductive material or combination of conductive materials, e.g., at least one of copper, silver, titanium, niobium, zirconium, tantalum, stainless steel, platinum, iridium, aluminum, Kovar, or nickel (including clad structures, laminates etc.). In one or more embodiments, the external contact 34 can include two or more materials, e.g., bi-metals, clad laminates, etc.

Further, the external contact 34 can take any suitable shape or shapes. In one or more embodiments, the external contact 34 can take a circular shape in a plane parallel to the first major surface 14 of the substrate 12 as shown in FIG. 2. In one or more embodiments, the external contact 34 can take a rectangular shape in the plane parallel to the first major surface 14 of the substrate 12. Further, the external contact 34 can take any suitable shape or shapes in a plane orthogonal to the first major surface 14 of the substrate 12, e.g., square, tapered, domed, etc. In one or more embodiments, the external contact 34 can take substantially the same shape as an external contact of one or more additional feedthroughs 18. In one or more embodiments, external contact 34 can take a shape that is different from the shape of an external contact of one or more additional feedthroughs 18. Further, in one or more embodiments, one or more external contacts 34 can include complex shapes such as grooves or channels formed in the contact to facilitate attachment of conductors or electronic devices to the contacts.

The external contact 34 can also include any suitable dimensions. In one or more embodiments, the contact 34 can have any suitable thickness in a direction normal to the first major surface 14 of the substrate 12. It is envisioned that for purposes of this disclosure, the dimension of the external contact's thickness is limited only by the fabrication techniques. With that in mind, in one or more example embodiments, a typical thickness can be at least 2 micrometers. In other example embodiments, it may be desirable to have the thickness be less than 10 millimeters, although greater thicknesses are also contemplated in accordance with embodiments of the disclosure. The thickness of the contact 34 can be the same as or different from the thickness of an external contact of one or more additional feedthroughs. In one or more embodiments, the external contact 34 can be of sufficient size and thickness to enable laser, resistance, or other welding and joining techniques to be utilized to electrically couple conductors and/or electronic devices to the external contact.

In one or more embodiments, the external contact 34 can be formed or disposed over the via 30 on the first major surface 14 of the substrate 12. For purposes of the present disclosure, the terms "form," forming," and "formed" will be used interchangeably with the terms "dispose," "disposing," and "disposed" respectively, such that the terms are considered to be equivalent. In other words, the external contact 34 is disposed over the via 30 such that the contact covers the via and the via is not visible in a plan view of the first major surface 14 of the substrate 12. In one or more embodiments, the external contact 34 (or any of the external contacts described herein) can be formed separately from the substrate 12 as a discrete member, or it could be patterned from a conductive sheet or foil.

The external contact 34 is electrically coupled to the conductive material 32 that is disposed in the via 30. In one or more embodiments, the external contact 34 is in direct contact with the conductive material 32 to electrically couple the contact to the conductive material. In one or more embodiments, one or more additional conductive layers (e.g., interlayer 40) can be disposed between the external contact 34 and the conductive material 32 to electrically couple the external contact to the conductive material.

In one or more embodiments, the external contact 34 is hermetically sealed to the first major surface 14 of the substrate 12. Any suitable technique or techniques can be utilized to hermetically seal the external contact 34 to the first major surface 14 of the substrate 12. For example, in one or more embodiments, the external contact 34 can be hermetically sealed to the first major surface 14 of the substrate 12 by a bond 35 that surrounds the via 30 as shown in FIG. 2. Any suitable technique or techniques can be utilized to form this bond 35. For example, in one or more embodiments, the bond 35 can be formed using a laser to provide a laser bond. By surrounding the via 30 with the bond 35 that hermetically seals the external contact 34 to the first major surface 14 of the substrate 12, the via is also protected from the external environment. The electrical coupling between the external contact 34 and the conductive material 32 disposed in the via 30 is, therefore, protected, and the integrity of this electrical pathway from the first major surface 14 of the substrate to the second major surface 16 can be maintained. In one or more embodiments, the external contact 34 can also be attached to the first major surface 14 of the substrate 12 using bonds in addition to bond 35. For example, in one or more embodiments, the external contact 34 can be attached to the first major surface 14 by bond 35 and one or more additional bonds between the external contact 34 and the first major surface, e.g., point bonds.

In one or more embodiments, the feedthrough 18 can include an internal contact 36 disposed adjacent the second major surface 16 of the substrate 12. As used herein, the term "adjacent the second major surface of the substrate" means that an element or component is disposed closer to the second major surface than to the first major surface of the substrate. The internal contact 36 can include any suitable material or materials, e.g., the same materials utilized for the external contact 34 or others, and can be formed using any suitable technique or techniques such as sputtering, plating, evaporating, etc. Further, the internal contact 36 can take any suitable shape or shapes and have any suitable thickness in a direction normal to the second major surface 16 of the substrate 12, e.g., the same shapes and thicknesses as described regarding the external contact 34, or other thicknesses and shapes such as conductive traces.

The internal contact 36 is disposed over the via 30 on the second major surface 16 of the substrate 12. The contact 36 can be electrically coupled to the conductive material 32 disposed in the via 30. The arrangement 30 of the external contact 34, the via 30 and the internal contact 36 facilitates creation of an electrical pathway between the external side adjacent to the first major surface 14 and the interior side adjacent to the second major surface 16. In one or more embodiments, the internal contact 36 is hermetically sealed to the second major surface 16 of the substrate 12 using any suitable technique or techniques, e.g., by a bond (e.g., laser bond) that surrounds the via 30.

Connected to the first major surface 14 of the dielectric substrate 12 is the patterned layer 20. The patterned layer 20 can include any suitable conductive or nonconductive material or materials, e.g., at least one of copper, silver, titanium, niobium, zirconium, tantalum, stainless steel, platinum, iridium, aluminum, Kovar, or nickel. In the embodiment illustrated in FIGS. 1-2, the patterned layer 20 is a patterned conductive layer. In one or more embodiments, the patterned conductive layer 20 can include a foil or foils disposed using any suitable technique or techniques. The patterned conductive layer 20 can include any suitable layers or sublayers.

Further, the patterned conductive layer 20 can be disposed in any suitable pattern when connected to the first major surface 14 of the dielectric substrate 12. In one or more embodiments, one or more portions of the patterned conductive layer 20 can form one or more external contact 34 of one or more vias 18 disposed in the dielectric substrate 12. Further, the patterned conductive layer 20 can include one or more welding portions 28 that can be utilized to connect the ferrule 22 to the dielectric substrate 12 as is further described herein.

Any suitable technique or techniques can be utilized to dispose the patterned conductive layer 20 on or adjacent the first major surface 14 of the dielectric substrate 12. For example, the patterned conductive layer 20 can be disposed on or adjacent the first major surface 14 utilizing one or more of photolithography, etching, plasma vapor deposition, chemical vapor deposition, electroplating, laser bonding, etc. In one or more embodiments, the patterned conductive layer 20 can be connected to the first major surface 14 by one or more laser bonds 59.

In one or more embodiments, the assembly 10 can include a second patterned conductive layer 38 disposed on or adjacent the second major surface 16 of the dielectric substrate 12. The second patterned conductive layer 38 can include any suitable patterned conductive layer, e.g., patterned conductive layer 20. In one or more embodiments, one or more portions of the second patterned conductive layer 38 can provide one or more internal contact 36 of one or more feedthroughs 18. The same design characteristics and possibilities described herein regarding the first patterned conductive layer 20 can be applied to the second patterned conductive layer 38.

The patterned conductive layer 20 can include any suitable number of layers. For example, the patterned conductive layer 20 can include a conductive sublayer 60 and an interlayer 40 disposed between the conductive sublayer and the first major surface 14 of the dielectric substrate 12. The interlayer 40 can include any suitable material or materials, e.g., titanium, niobium, tantalum, zirconium, and alloys thereof. Further, the interlayer 40 can have any suitable dimensions. In one or more embodiments, the interlayer 40 can have a thickness as measured in a direction orthogonal to the first major surface 14 of the dielectric substrate 12 of at least 50 nanometers and no greater than 10 micrometers. The interlayer 40 can be disposed between the conductive sublayer 60 and the first major surface 14 of the dielectric substrate 12 using any suitable technique or techniques, e.g., the same techniques described herein regarding the patterned conductive layer 20. In one or more embodiments, the interlayer 40 and the conductive sublayer 60 can be disposed on the first major surface 14 of the substrate 12 and then patterned using any suitable technique or techniques. Further, the second patterned conductive layer 38 can include any suitable number of layers. Although not shown, the second patterned conductive layer 38 can include one or more conductive sublayers and interlayers disposed between the conductive sublayers and the second major surface 16 of the dielectric substrate 12. Any suitable interlayer or interlayers can be utilized, e.g., interlayer 40.

Connected to the dielectric substrate 12 is the ferrule 22. The ferrule 22 can include any suitable material or materials, e.g., at least one of titanium, niobium, or stainless steel. In one or more embodiments, the ferrule 22 can include a conductive material. The ferrule 22 can take any suitable shape or shapes and have any suitable dimensions.

For example, as shown in FIG. 2, the ferrule 22 can have an elliptical shape in a plane parallel to the first major surface 14 of the substrate 12. Further, the flange 26 can also take an elliptical shape in the plane parallel to the first major surface 14 of the substrate 12.

The ferrule 22 includes the body 24 and the flange 26 that extends from the body. The flange 26 can be integral with the body 24 or manufactured separately and attached to the body using any suitable technique or techniques. The flange 26 can include the same material or materials utilized to form the body 24. In one or more embodiments, the flange 26 and the body 24 can include different materials.

As mentioned herein, the ferrule 22 can be connected to the dielectric substrate 12 using any suitable technique or techniques. As illustrated in FIG. 1, the ferrule 22 is connected to the welding portion 28 of the patterned conductive layer 20 that is disposed between the flange 26 and the first major surface 14 of the dielectric substrate 12 such that the ferrule is hermetically sealed to the dielectric substrate. In one or more embodiments, the ferrule 22 can be connected to the second major surface 16 of the dielectric substrate 12. Further, in one or more embodiments, the ferrule 22 can be connected to the first major surface 14 and the second major surface 16 of the dielectric substrate, e.g., the ferrule can include a second flange (not shown) that can be connected to the second major surface of the dielectric substrate. In one or more embodiments, a major surface 42 of the flange 26 contacts the welding portion 28 of the patterned conductive layer 20 when the ferrule 22 is connected to the welding portion. In one or more embodiments, the major surface 42 of the flange 26 is substantially parallel to the first major surface 14 of the dielectric substrate 12. As used herein, the term "substantially parallel" means that an angle formed between the major surface 42 of the flange 26 and the first major surface 14 of the dielectric substrate 12 is less than 10 degrees. Further, a gap between the major surface 42 of the flange 26 and the first major surface 14 of the dielectric substrate 12 is compatible with the joining techniques utilized to connect the flange to the dielectric substrate.

The flange 26 can be welded to the welding portion 28 of the patterned conductive layer 20 using suitable technique or techniques. In one or more embodiments, the flange 26 is welded to the welding portion 28 of the patterned conductive layer 20 by a weld 44. Any suitable welding technique or techniques can be utilized to provide the weld 44, e.g., laser welding. Further, the weld 44 can take any suitable shape or shapes and have any suitable dimensions.

In one or more embodiments, the ferrule 22 can be electrically connected to the patterned conductive layer 20 using any suitable technique or techniques. As shown in FIG. 1, the assembly 10 includes a second feedthrough 46 disposed in the dielectric substrate 12 that is electrically connected to the flange 26 of the ferrule 22. The feedthrough 46 can include any suitable feedthrough, e.g., feedthrough 18. The feedthrough 46 includes a via 48 disposed between the first major surface 14 and the second major surface 16 of the dielectric substrate 12, and conductive material 50 disposed in the via. The conductive material 50 is electrically connected to the welding portion 28 of the patterned conductive layer 20 through the interlayer 40 if present. The welding portion 28 of the patterned conductive layer 20 is electrically connected to the flange 26 of the ferrule 22. The second feedthrough 46 also includes an internal contact 52 disposed adjacent the second major surface 16 of the dielectric substrate 12 and electrically connected to the conductive material 50 disposed in the via 48. As a result, the internal contact 52 is electrically connected to the ferrule 22.

The assembly 10 can also include one or more electronics or electronic components 54 disposed adjacent at least one of the first major surface 14 or the second major surface 16 of the dielectric substrate 12. The electronic component 54 can include any suitable circuit or component, e.g., at least one of a capacitor, transistor, integrated circuit, including controller or multiplexer, sensor, accelerometer, optical components such as emitters and detectors, etc. Although depicted as including one electronic component 54, the assembly 10 can include any suitable number of electronic components. Further, the electronic component 54 can be electrically connected to one or more feedthroughs 18 using any suitable technique or techniques. In one or more embodiments, the electronic component 54 is electrically connected to one or more feedthroughs 18 by one or more device contacts 56. Such device contacts 56 can be electrically connected to one or more internal contacts 36 of feedthroughs 18 using any suitable technique or techniques. In one or more embodiments, the electronic component 54 can include one or more test points (e.g., one or more test points 362 of FIG. 8) disposed on one or surfaces of the electronic component as is further described herein.

As mentioned herein, one or more embodiments of assembly 10 can include the patterned conductive layer 20 that is connected (e.g., hermetically sealed) to the first major surface 14 of the dielectric substrate 12 using any suitable technique or techniques, e.g., welding, laser welding, laser bonding, diffusion bonding, laser-assisted diffusion bonding, etc. In one or more embodiments, the patterned conductive layer 20 can be connected to the first major surface 14 using the laser diffusion bonding techniques described in co-owned U.S. Pat. No. 10,124,559 B2, entitled KINETICALLY LIMITED NANO-SCALE DIFFUSION BOND STRUCTURES AND METHODS. For example, electromagnetic radiation (e.g., light) can be directed through the second major surface 16 of the dielectric substrate 12 and focused at an interface between the patterned conductive layer 20 and the first major surface 14 to form the laser bond 59 and laser bonds 35 of the external contacts 34. In embodiments where the interlayer 40 is present, the electromagnetic radiation can be focused at an interface between the interlayer and the first major surface 14.

Any suitable electromagnetic radiation can be utilized to form a bond between one or more portions of the patterned conductive layer 20 and the first major surface 14 of the dielectric substrate 12. In one or more embodiments, the electromagnetic radiation can include laser light that can include any suitable wavelength or range of wavelengths. In one or more embodiments, the laser light can include light having a wavelength of at least 200 nm. In one or more embodiments, the laser light can include a wavelength of no greater than 10,000 nm. For example, laser light can include UV light, visible light, IR light, and combinations thereof. In one or more embodiments, a UV laser can be utilized to provide light having a wavelength of about 350 nm and a pulse width of 30 ns. In one or more embodiments, the materials for the substrate 12 and the patterned conductive layer 20, and the power level and wavelength of the light used may be selected such that the light may not directly damage, ablate, warp, or cut the substrate and the patterned conductive layer, and such that the substrate and the patterned conductive layer retain their bulk properties.

In general, light can be provided by any suitable laser or laser system. For example, the laser may generate light having a relatively narrow set of wavelengths (e.g., a single wavelength). The light emitted by the laser may form a collimated beam that may not be focused at a particular point. The light emitted by the laser may be focused at interfaces between the patterned conductive layer 20 and the first major surface 14 to generate a laser bond.

Although the laser may provide light that has a narrow range of wavelengths, in one or more embodiments, the laser may represent one or more devices that emit light having a wider range of wavelengths than a single typical laser. A wide variety of devices may be used to emit light having a narrow or wide range of wavelengths. In one or more embodiments, the laser may include one or more laser devices including diode and fiber lasers. Laser sources may also include, e.g., TI sapphire, argon ion, Nd:YAG, XeF, HeNe, Dye, GaAs/AlGaAs, $CO_2$, Alexandrite, InGaAs, InGaAsP, Nd:glass, Yb:YAG, or Yb fiber lasers. The laser device may also include one of continuous wave, modulated, or pulsed modes. Accordingly, a wide variety of laser devices may be used in the bonding process. In one or more embodiments, a power level of the laser may be set to approximately 1 W, distributed across the approximate focused beam diameter of 10 μm, with a top hat or Gaussian spatial energy profile.

Figure 3:
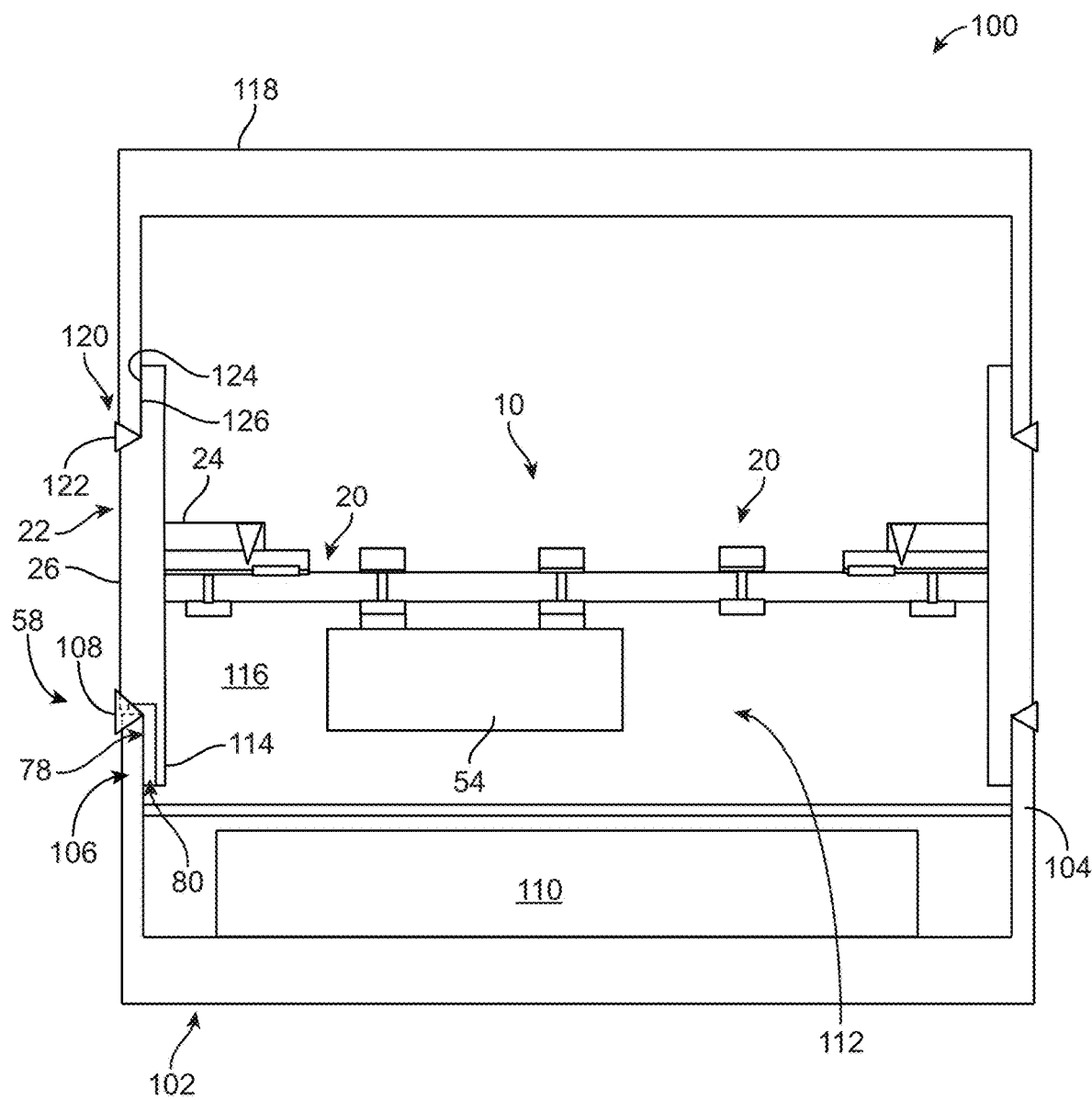
FIG. 3 is a schematic cross-section view of a hermetically-sealed package that includes the hermetic assembly of FIG. 1.

As mentioned herein, the various embodiments of feedthrough assemblies can be utilized in any suitable device or system. For example, FIG. 3 is a schematic cross-section view of one embodiment of a hermetically-sealed package 100. The package 100 includes a housing 102 and the hermetic assembly 10 of FIG. 1. Although depicted as including the hermetic assembly 10 of FIG. 1, the hermetically-sealed package 100 can include any suitable hermetic assembly. In one or more embodiments, the hermetic assembly 10 can form a part of the housing 102. The housing 102 defines a recess 112 within which one or more electronic components or circuitry (e.g., electronic component 54) can be disposed. Further, the housing 102, ferrule 22, and dielectric substrate 12 form a cavity 116.

The housing 102 of the package 100 can include any suitable dimensions and take any suitable shape or shapes. In general, the housing 102 is sized and shaped to at least partially surround the electronic device 54. In one or more embodiments, the housing 102 can include one or more sidewalls 104 that can be connected to the hermetic assembly 10 using any suitable technique or techniques as is further described herein. The housing 102 can completely surround and enclose the electronic device 54, and the hermetic assembly 10 can be connected to the housing. In one or more embodiments, the housing 102 can include an open side or face, and the hermetic assembly 10 can be connected to the housing within this open side such that the hermetic assembly forms a part of the housing. The housing 102 can be a unitary housing or can include one or more sections that are joined together using any suitable technique or techniques.

The housing 102 can include any suitable material or materials, e.g., metal, polymeric, ceramic, or inorganic materials. In one or more embodiments, the housing 102 can include at least one of glass, quartz, silica, sapphire, silicon carbide, diamond, synthetic diamond, or gallium nitride (including clad structures, laminates etc.). In one or more embodiments, the housing 102 can include at least one of copper, silver, titanium, niobium, zirconium, tantalum, stainless steel, platinum, iridium, aluminum, nickel, Kovar, or AlMg (including clad structures, laminates etc.). In one or more embodiments, the housing 102 can include the same material or materials as the dielectric substrate 12 of the hermetic assembly 10.

The package 100 can include any suitable electronic component 54 or electronics disposed within the housing 102. In one or more embodiments, the electronic component 54 can include any suitable integrated circuit or device, e.g., a controller, a multiplexer, etc. It should be understood that any of the electronic devices mentioned in this disclosure can be coupled to a power source. Further, the package 100 can include a second electronic component 110 disposed in any suitable location within the housing 102. The second electronic component 110 can include any suitable integrated circuit or device. In one or more embodiments, the second electronic component 110 can include a power source that is adapted to provide power to one or more integrated circuits or devices disposed within the housing 102 or exterior to the housing. Any suitable power source 110 can be disposed within the housing 102, e.g., one or more batteries, capacitors, etc. The power source 110 can be rechargeable by electrically connecting the power source to a power supply through the hermetic assembly 10. In one or more embodiments, the power source 110 can be adapted to be inductively charged by an inductive power system that is external to the package 100. The power source 110 can be electrically connected to the electronic component 54 using any suitable technique or techniques. In one or more embodiments, the power source 110 can include a hermetically-sealed battery that is connected to the hermetic assembly 10 using any suitable technique or techniques.

The housing 102 can be connected to the hermetic assembly 10 using any suitable technique or techniques. In the embodiment illustrated in FIG. 3, an edge 58 of the body 26 of the ferrule 22 is connected to an edge 106 of the housing 102 by a bond or weld 108. Any suitable technique or techniques can be utilized to form the weld 108, e.g., the same techniques described herein regarding the weld 44 between the flange 24 and the welding portion 28 of the patterned conductive layer 20. Further, the ferrule 22 can include an overhang 114 that is disposed adjacent the edge 106 of the housing 102. In one or more embodiments, the overhang 114 can be adapted to block energy utilized to form weld 108 from damaging electronic component 54.

As mentioned herein, the ferrule 22 of the hermetic assembly 10 can be electrically connected to the patterned conductive layer 20 via the welding portion 28 of the patterned conductive layer. As a result, the patterned conductive layer 20 can also be electrically connected to the housing 102 of the package 100 via the ferrule 22 and its connection to the housing. In one or more embodiments, the ferrule 22 can be electrically connected to a ground terminal that is, e.g., on the housing 102 of the package 100.

The ferrule 22 of the assembly 10 can also include a slot 78 disposed in the body 26 of the ferrule. In one or more embodiments, the slot 78 can extend along the edge 58 and overhang 114 of the body 26 of the ferrule. The slot 78 can take any suitable shape or shapes and have any suitable dimensions. When the assembly 10 and the housing 102 are connected together, the slot 78 can be adapted to form a vent 80 with the edge 106 of the housing. In one or more embodiments, the slot 78 can be adapted to form the vent 80 with the edge 106 and the sidewalls 104 of the housing 102. The vent 80 can allow backfill gas exchange of the package 100 before the assembly 10 is sealed to the housing 102. Once gas exchange is completed, the vent 80 can be sealed with weld 108.

Figure 15:
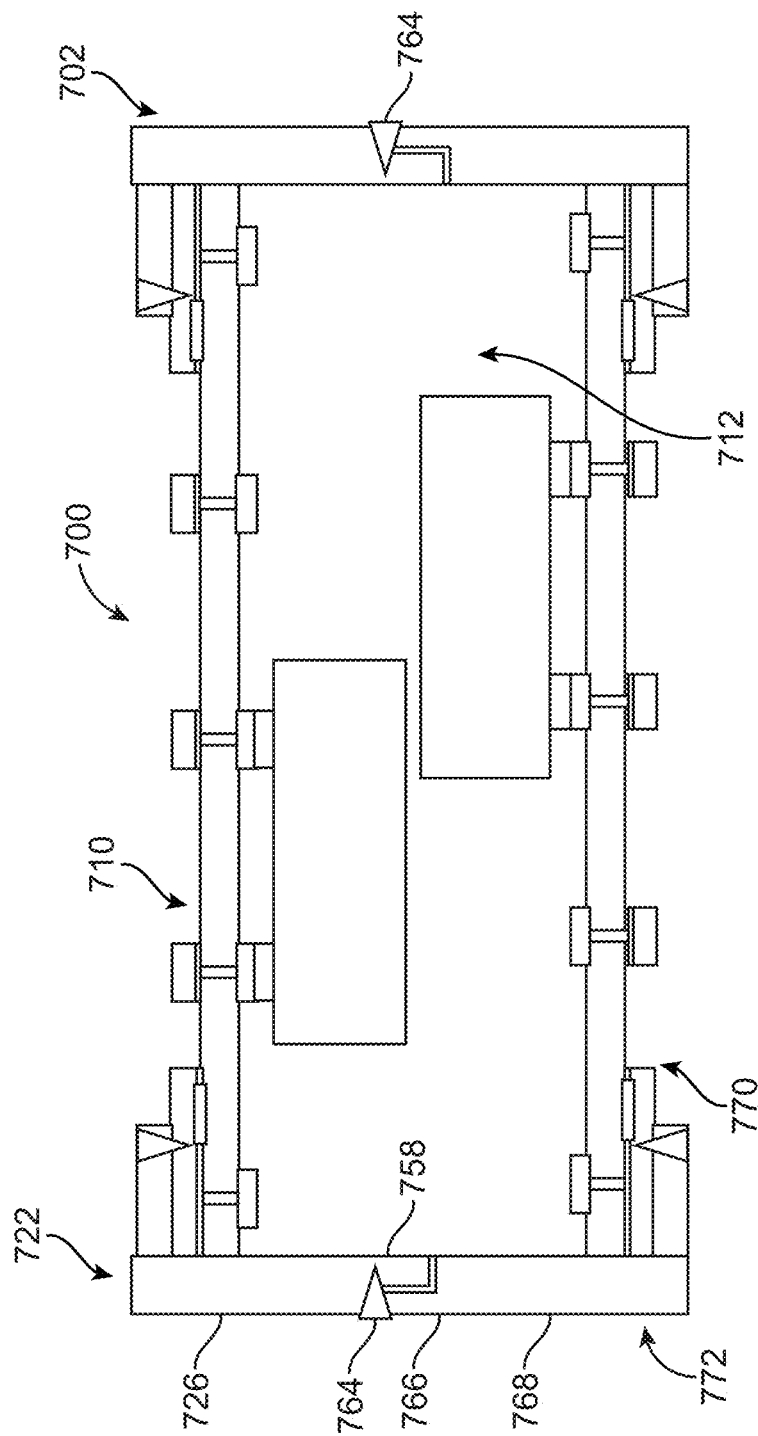
FIG. 15 is a schematic cross-section view of another embodiment of a hermetically-sealed package.
Figure 16:
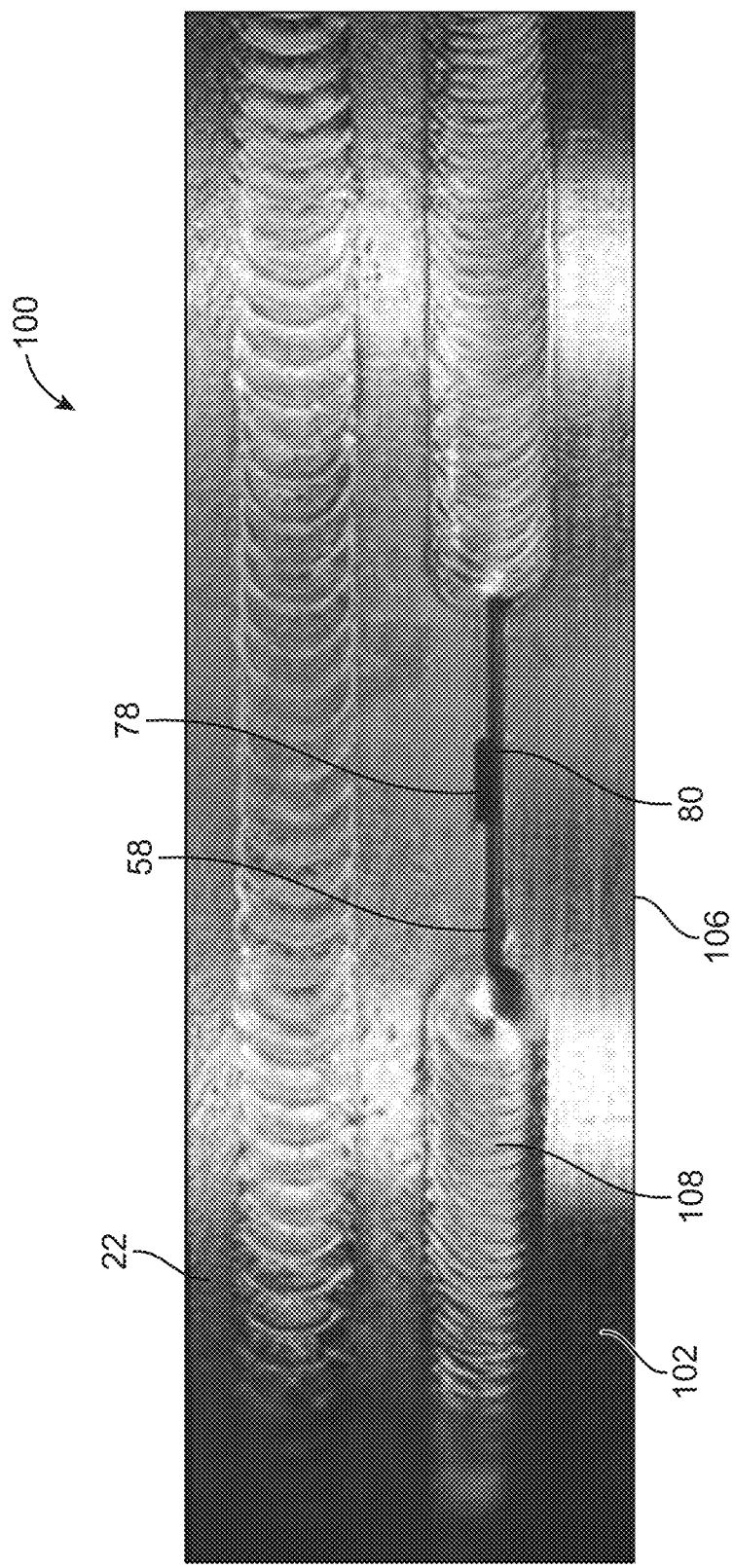
FIG. 16 is a schematic side view of a portion of the hermetically-sealed package of FIG. 3.

For example, FIG. 15 is a schematic plan view of an outer portion of the package 100. As can be seen in FIG. 15, a substantial portion of the edge 58 of the body 26 of the ferrule 22 is connected to the edge 106 of the housing 102 by the weld 108. A portion of the edges 58, 106 are, however, left unwelded such that the vent 80 is exposed. Gas exchange of the package 100 through the vent 80 can be performed. After gas exchange has been completed, the weld 122 can be completed over the remainder of edges 58, 106 and the vent 80 to seal the ferrule 22 to the housing 102.

In one or more embodiments, the package 100 can include an optional second housing 118 connected to a second edge 120 of the body 26 of the ferrule 22. All of the design considerations and possibilities regarding the housing 102 apply equally to the second housing 118. The second housing 118 can be any suitable structure or component to which the assembly 10 is connected. In one or more embodiments, the second housing 118 can include a header of an implantable medical device (e.g., header 330 of FIGS. 5-8). The second housing 118 can include the same materials as the housing 102 or different materials.

The second housing 118 can be connected to the second edge 120 of the ferrule 22 using any suitable technique or techniques, e.g., the same techniques described herein regarding the connection of the housing 102 to the ferrule. In one or more embodiments, the second housing 118 can be connected to the ferrule 22 by a weld 122 that is disposed through the second housing and into the ferrule. Further, the second edge 120 of the ferrule 22 can include a second overhang 124 that is disposed adjacent an edge 126 of the second housing 118.

The second housing 118 can be electrically connected to the ferrule 22 using any suitable technique or techniques. In one or more embodiments, the second housing 118 can be electrically connected to the hermetic assembly 10 through the electrical connection of the ferrule 22 to the patterned conductive layer 20. Further, the second housing 118 can be electrically connected to the housing 102 via the ferrule 22.

Figure 4:
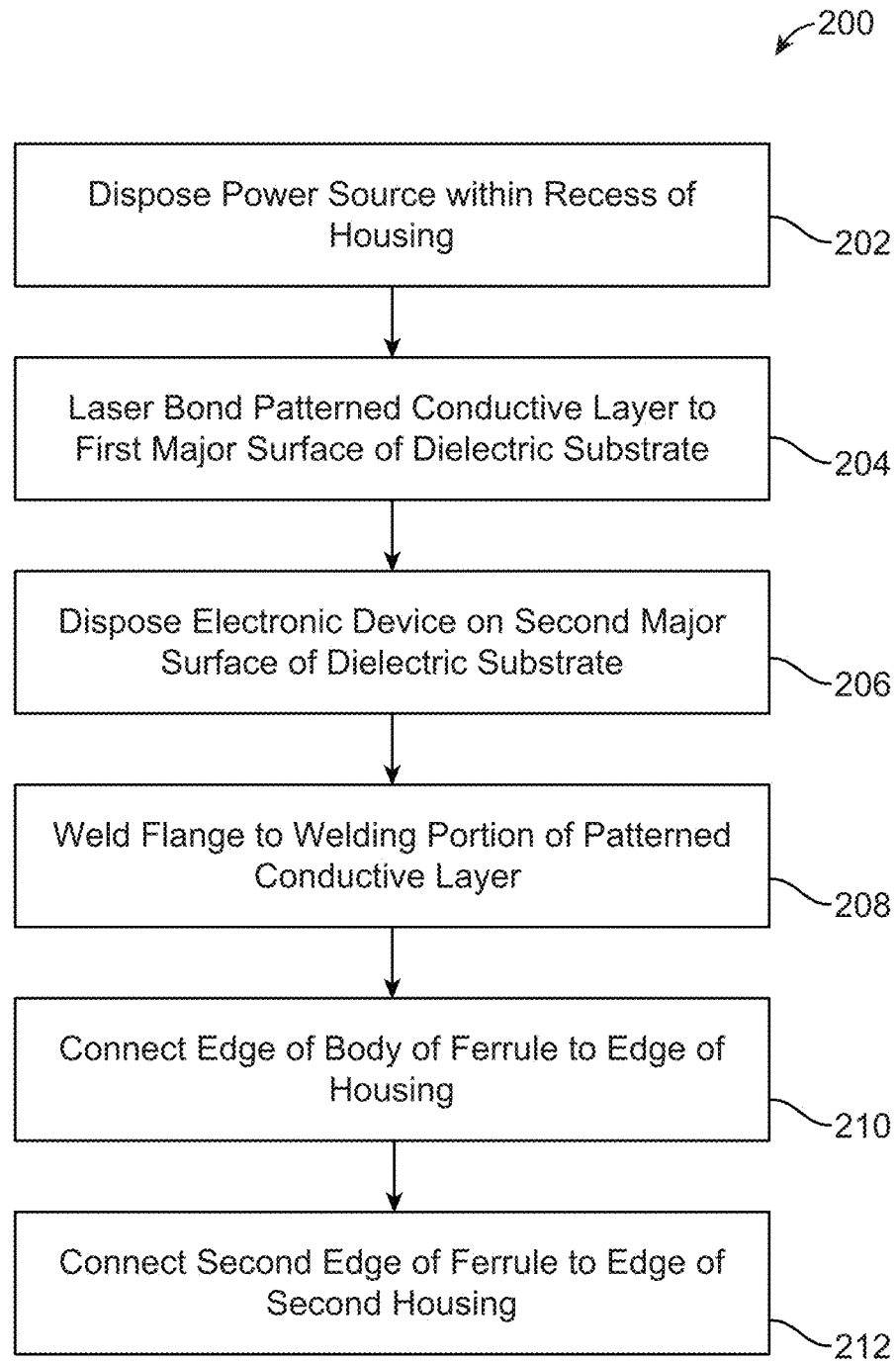
FIG. 4 is a flowchart of one embodiment of a method of forming the hermetically-sealed package of FIG. 3.
Figure 5:
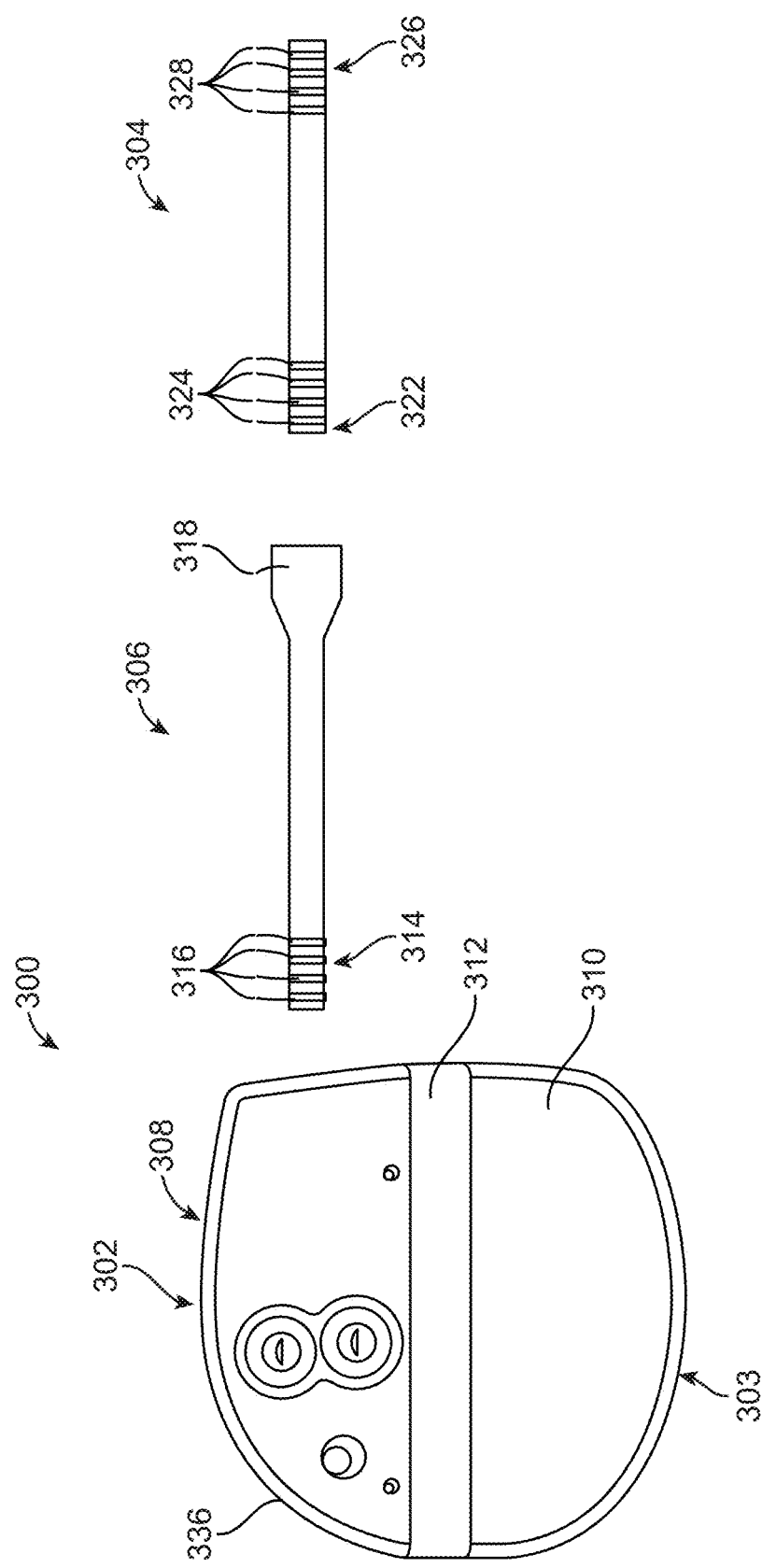
FIG. 5 is a schematic side view of one embodiment of an implantable medical device.

The package 100 can be manufactured using any suitable technique or techniques. For example, FIG. 4 is a flowchart of one embodiment of a method 200 of forming the hermetically-sealed package 100. Although described in regard to the package 100, the method 200 can be utilized to form any suitable hermetically-sealed package.

Method 200 includes disposing the power source 110 within the recess 112 of the housing 102 at 202. In one or more embodiments, the power source 110 can be a hermetically-sealed battery that has been formed within housing 102 using any suitable technique or techniques. The patterned conductive layer 20 can be laser bonded to the first major surface 14 of the dielectric substrate 12 at 204. Further, at 206, the electronic device 54 can be disposed on the second major surface 16 of the dielectric substrate 12. At 208, the flange 26 of the ferrule 22 can be welded to the welding portion 28 of the patterned conductive layer 20 such that the welding portion is between the flange and the first major surface 14 of the dielectric substrate 12 and the ferrule is hermetically sealed to the dielectric substrate. Further, the edge 58 of the body 26 of the ferrule 22 can be connected to the edge 106 of the housing 102 (or hermetically-sealed battery) at 210 using any suitable technique or techniques such that the electronic device 54 is disposed within cavity 116. In one or more embodiments, the weld 108 can be formed between the ferrule 22 and the housing 102 using any suitable technique or techniques. In one or more embodiments, the weld 108 hermetically-seals the assembly 10 to the housing 102.

When the ferrule 22 includes the slot 78, a portion of the edges 58, 106 can remain disconnected such that the vent 80 is exposed. In such embodiments, the method 200 can include a gas exchange between the package 100 and the environment external to the package. Any suitable gas exchange technique or techniques can be utilized. In one or more embodiments, a vacuum can be applied to the package 100 such that any internal gases or ambient air can be removed from the package. Optionally, the package 100 can be subjected to heat while under vacuum to remove any moisture from within the package. In one or more embodiments, the package 100 can be backfilled by exposing the package to an inert or low-reactive gas such as argon, nitrogen, helium, or combinations thereof, such that the gas enters the package through the vent 80. While still in an inert gas environment, the weld 108 can be disposed over the vent 80 and between the remainder of the edge 58 of the body 26 of the ferrule 22 and the edge 106 of the housing 102 such that the assembly 10 is hermetically sealed to the housing.

In embodiments where the hermetically-sealed package 100 includes second housing 118, the edge 126 of such housing can be connected to the second edge 120 of the body 26 of the ferrule 22 at 212 using any suitable technique or techniques. In one or more embodiments, the weld 122 can be formed through the edge 126 of the second housing 118 and into the second edge 120 of the body 26 of the ferrule 22. In one or more embodiments where the second housing 118 is a header (e.g., header 308 of FIGS. 5-8), the header can be connected to the second edge 120 of the body 26 of the ferrule 22 such that the header is electrically connected to the feedthrough 20 of hermetic assembly 10 using any suitable technique or techniques. In one or more embodiments, the gas exchange through vent 80 can occur prior to or after the second housing 118 is connected to the second edge 120 of the body 26 of the ferrule 22.

The various embodiments of feedthrough assemblies described herein can be utilized with any device or system that requires hermetically sealed conductive pathways. For example, one or more embodiments of feedthrough assemblies described herein can be utilized with an implantable medical device or system. In one or more embodiments, the implantable medical device or system can employ one or more leads that may be used with the various embodiments of feedthrough assemblies described herein. Representative examples of such implantable medical devices include hearing implants, e.g., cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators; or the like. Further, in one or more embodiments, an implantable medical device can include one or more external contacts of a hermetic assembly that can be utilized to directly provide energy to tissue of a patient.

For example, FIGS. 5-8 are various schematic views of one embodiment of an implantable medical device system 300. The system 300 includes an implantable medical device (IMD) 302, a lead 304, and a lead extension 306.

The IMD 302 includes a hermetically-sealed package 303 that includes a housing 310, a hermetic (e.g., feedthrough) assembly 312 that forms a part of the housing, and a header 308 adapted to receive a proximal portion 314 of the lead extension 306. All of the design considerations and possibilities regarding the hermetically-sealed package 100 of FIG. 3 apply equally to the hermetically-sealed package 303 of IMD 302. Although depicted as include a single hermetic assembly 312, the IMD 302 can include any suitable number of hermetic assemblies.

The proximal portion 314 of lead extension 306 includes one or more electrical contacts 316 that are electrically connected to internal contacts (not shown) at distal connector 318 of the lead extension. The header 308 of the IMD 302 includes internal contacts 320 (FIGS. 6-7) and is adapted to receive the proximal portion 314 of the lead extension 306 such that the internal contacts of the header may be electrically connected to the contacts 316 of the lead extension when the lead extension is inserted into the header.

The system 300 depicted in FIGS. 5-8 further includes lead 304. The depicted lead 304 has a proximal portion 322 that includes contacts 324 and a distal portion 326 that includes electrodes 328. Each of the electrodes 328 can be electrically connected to a discrete contact 324. The distal connector 318 of the lead extension 306 is adapted to receive the proximal portion 322 of the lead 304 such that the contacts 324 of the lead can be electrically connected to the internal contacts of the connector of the extension. Accordingly, a signal generated by the IMD 302 can be transmitted to tissue of a patient by an electrode 328 of lead 304 when the lead is connected to the extension 306 and the extension is connected to the IMD. In one or more embodiments, a signal received by electrode 328 of lead 304 from the patient may be transmitted to a contact 320 of the IMD 302 when the lead is connected to the extension 306 and the extension is connected to the IMD.

It will be understood that lead 304 can be connected to IMD 302 without use of an extension 306. Any number of leads 304 or extensions 306 can be connected to device 302. While lead 304 is depicted as having four electrodes 328, it will be understood that the lead can include any number of electrodes, e.g. 1, 2, 3, 4, 5, 6, 7, 8, 16, 32, or 64 electrodes. Corresponding changes in the number of contacts 324 in lead 304, contacts 316 and internal contacts in connector 318 of lead extension 306, or internal contacts 320 in header 308 of device 302 may be required or desired. As used hereinafter, "lead" will refer to both "leads" and "lead extensions" unless the content and context clearly dictates otherwise.

The IMD 302 further includes the hermetically sealed package 303 in which electronics 334 are disposed. The housing 310 of the hermetically-sealed package 303 can include any suitable material or combination of materials, e.g., titanium, glass, sapphire, etc. In one or more embodiments, the housing 310 can be electrically conductive to provide a ground electrode for the IMD 302 as is known in the art.

Lead receptacles 330, 332 can be formed in the housing 336 of the header 308. The receptacles 330, 332 can take any suitable shape or shapes and have any suitable dimensions. Although depicted as including two receptacles 330, 332, the header 308 can include any suitable number or receptacles, e.g., 1, 2, 3, 4, or more receptacles. Further, the receptacles 330, 332 can be adapted to receive and electrically connect contacts 316 of the lead extension 306 (or contacts 324 of the lead 304) to contacts 320 of the header 308. Any suitable number of leads 304 and lead extension 306 can be electrically connected to the header 308 via the receptacles 330, 332.

Figure 6:
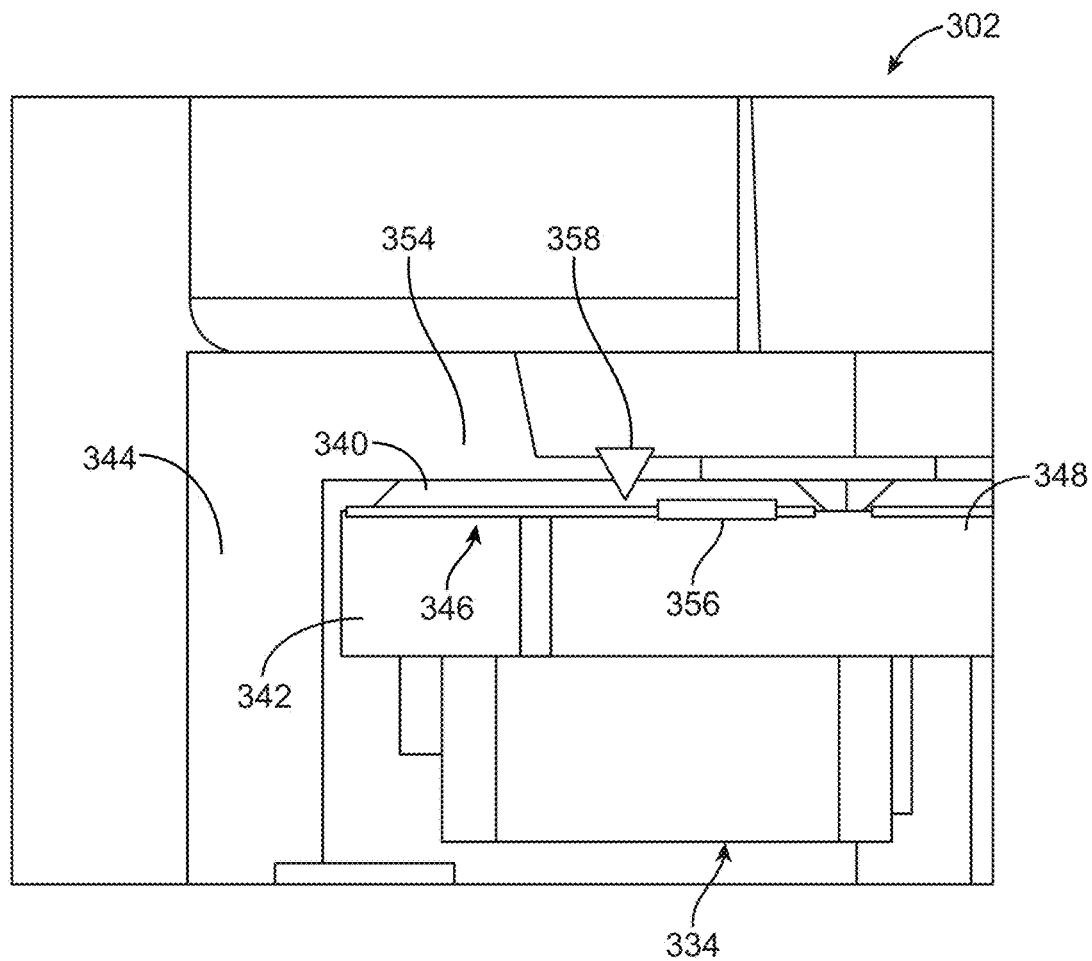
FIG. 6 is a schematic cross-section view of a portion of a hermetically-sealed package of the implantable medical device of FIG. 5.
Figure 7:
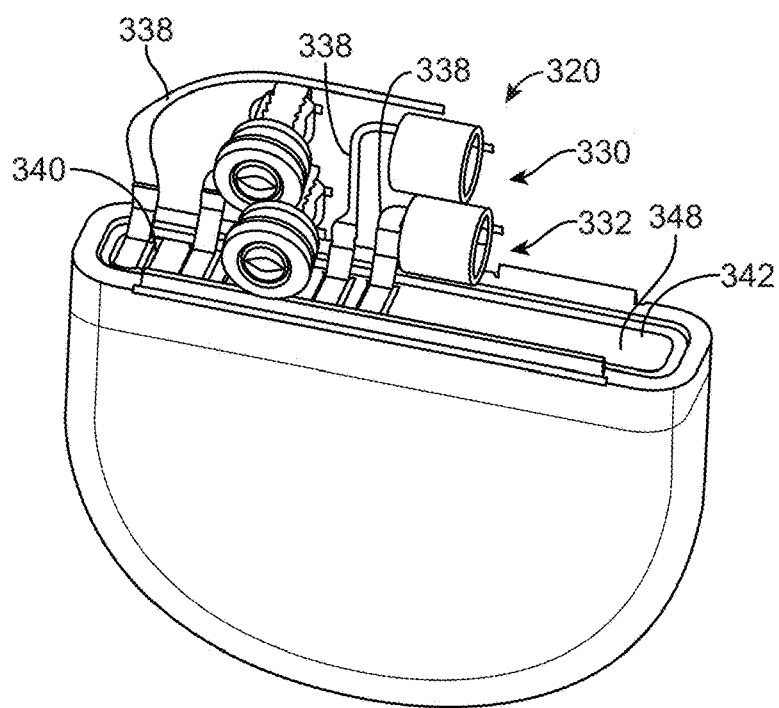
FIG. 7 is a schematic perspective cross-section view of the hermetically-sealed package of the implantable medical device of FIG. 5.

The receptacles 330, 332 have internal contacts 320 positioned to align with and electrically connect with contacts 316 of the lead extension 306 and/or contacts 324 of the lead 304 when the lead extension or lead is properly inserted into one or both receptacles. The pitch of the internal contacts 320 of FIG. 6 is adapted to allow electrical connection with the contacts 316 of the lead extension 306 or contacts 324 of the lead 304.

Electronics 334 disposed within the package 303 are adapted to send electrical signals to tissue of the patient, or receive signals from tissue of the patient, through leads operably coupled to the electronics of the IMD 302. As used herein, the term "transmitted electrical signals" is used to refer to both the signals sent by electronics 334 to tissue of the patient or received by the electronics from the tissue of the patient. In one or more embodiments, conductors of IMD 302 can be electrically connected to internal contacts 320 of lead receptacles 330, 332 via conductors 338 of hermetic assembly 312 that are electrically connected to a patterned conductive layer 340 of the assembly. For example, in one or more embodiments, conductors 338 can be electrically connected to the electronics 334 via a feedthrough that is disposed in a dielectric substrate 342 of the hermetic assembly 312. In one or more embodiments, one or more conductors can be electrically connected to a patterned conductive layer disposed on a second major surface of the dielectric substrate 342 using any suitable technique or techniques. The feedthrough can include any suitable feedthrough described herein, e.g., feedthrough 18 of assembly 10 of FIG. 1. A conductive pathway is, therefore, formed between the internal contacts 320 of lead receptacles 330, 332 and electronics 334. Hermetic assembly 312 can include any hermetic assembly described herein, e.g., hermetic assembly 10 of FIGS. 1-3.

In one or more embodiments, each conductor 338 can electrically connect an internal contact 320 of the lead receptacles 330, 332 to a discrete channel of the electronics 334. As used herein, a "channel" of the electronics is a discrete electronic pathway through which signals may be transmitted independently of another channel. Each channel of the electronics 334 can be independently connected with a discrete internal contact 320 of the receptacles 330, 332, which can be connected with a discrete contact 316 of the lead extension 306 or contact 324 of the lead 304, which can in turn be connected with a discrete electrode 328 of the lead. Accordingly, each channel of the electronics 334 can be operably connected to a given electrode 328 of the lead 304.

Figure 8:
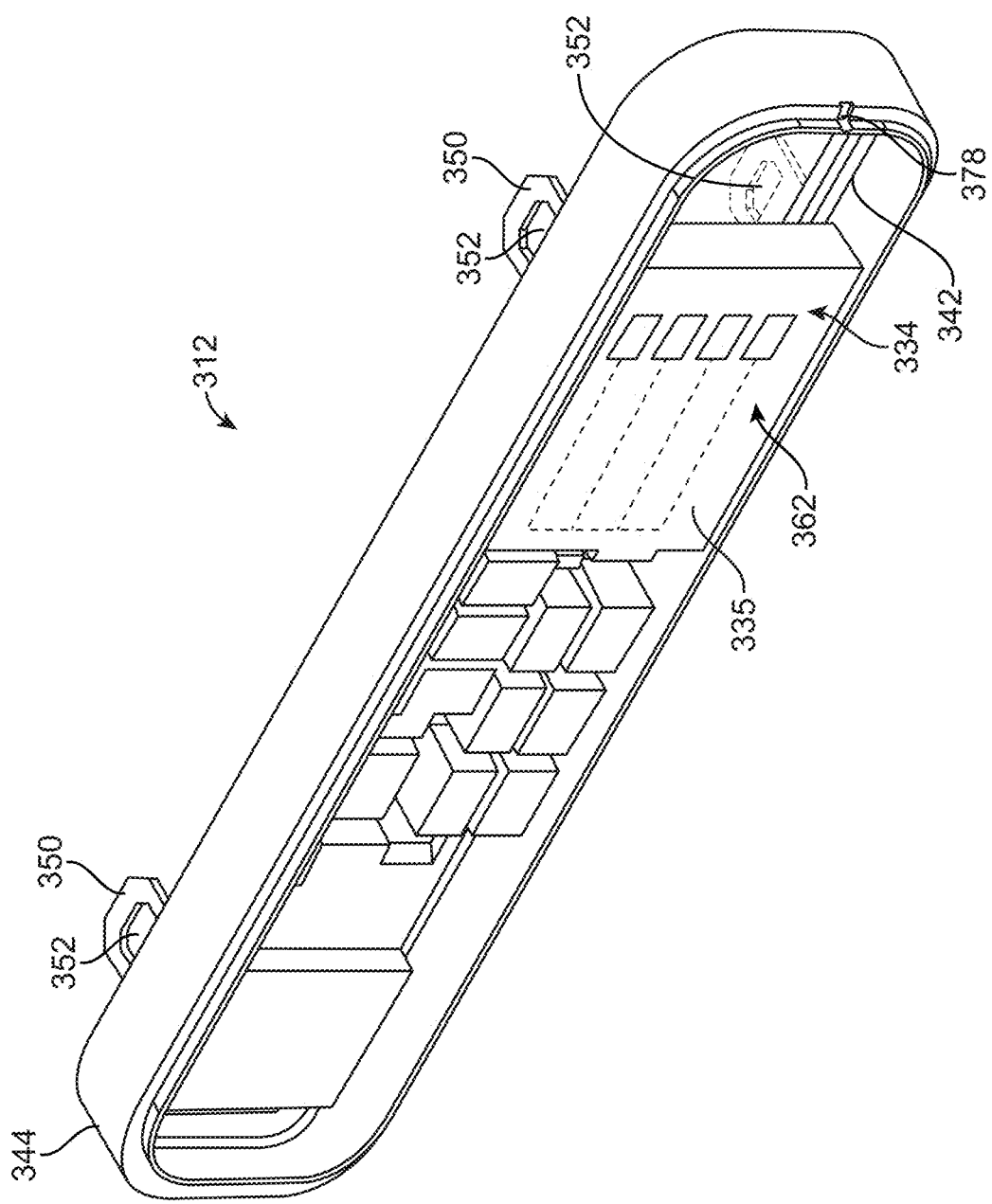
FIG. 8 is a schematic bottom perspective view of a hermetic assembly of the hermetically-sealed package of FIG. 7.

As shown in FIG. 8, one or more test points 362 can be disposed on a surface 335 of the electronics 334 (i.e., electronics package or component). such test points 362 can be utilized to test the electronics 334. The test points 362 can be incorporated into the electronics 334 as part of a three-dimensional die stack of the electronics package. Although not shown, vertical interconnects such as vias can be disposed through one or more of the electronics 334 and electrically connected to the test points 362. The surface 335 can be a non-functional surface such as glass with the test points 362 disposed on the surface and one or more vias disposed through the surface and into the layers of the electronics. In one or more embodiments, the surface 335 of the electronics 334 can be an active surface with the test points 362 disposed directly onto such active surface or on a redistribution layer disposed on the active surface. The test points 362 can be utilized to access schematic nodes disposed in a top layer or intermediate layers of the package of electronics 334 or to access schematic nodes disposed on the substrate 342 that are not disposed within the package.

Such placement of the test points 362 can reduce or eliminate the need for hybrid test points. Further, because the test points 362 are on or in the electronics stack, interconnections for such test points do not significantly increase the complexity of the stack. Further, such positioning of the test points 362 can reduce routing lengths to out-board test points, reduce EMI concerns, and simplify manufacturing. Further, the test points 362 can simplify burn-in when testing both in panel/wafer form and downstream when the devices are singulated. Also, troubleshooting completed devices can be simplified because the test points 362 remain formed on the electronics 334.

As is also shown in FIG. 8, a ferrule 344 of the hermetic assembly 312 can include an optional slot 378. The slot 378 can take any suitable shape or shapes and have any suitable dimensions. The slot 378 can be utilized to form a vent with the housing 336 to allow for gas exchange between the package 303 and the environment surrounding the package as is described herein regarding slot 78 and vent 80 of FIG. 3.

The hermetic assembly 312 can be disposed within the header 308 such that the housing 336 surrounds the assembly, and the assembly can be connected to a sidewall of the housing 310 of the IMD 302 between the header and the housing. In one or more embodiments, the hermetic assembly 312 can be disposed on any sidewall of the housing 310 such that the system does not include a header. In one or more embodiments, the hermetic assembly 312 can be connected to the housing by the ferrule 344 that is connected to a welding portion 346 of the patterned conductive layer 340 that is disposed between a flange 354 of the ferrule and a first major surface 348 of the dielectric substrate 342 such that the ferrule is hermetically sealed to the dielectric substrate. Any suitable technique or techniques can be utilized to hermetically seal the ferrule 344 to the dielectric substrate 342, e.g., the same techniques described herein regarding the hermetically-sealed package 100 of FIG. 3. For example, the patterned conductive layer 340 can be connected to the first major surface 348 of the dielectric substrate 342 by a laser bond 356. And the flange 354 of the ferrule 344 can be welded to the welding portion 346 of the patterned conductive layer 340 by weld 358 such that the ferrule is hermetically sealed to the dielectric substrate. Further, the hermetic assembly 312 can be disposed on a sidewall of the housing 310 using any suitable technique or techniques, e.g., the same techniques described herein regarding hermetically-sealed package 100 of FIG. 3.

The header 308 can be connected to at least one of the hermetic assembly 312 and the housing 310 using any suitable technique or techniques, e.g., the same techniques described herein regarding the hermetically-sealed package 100 of FIG. 3. In one or more embodiments, the hermetic assembly 312 can include tabs 350 (FIG. 8) that can receive one or more fasteners that extend through openings in the header 308 and openings 352 in the tabs and connect the header to the hermetic assembly. Any suitable fasteners can be utilized to connect the header 308 to the hermetic assembly 312.

Figure 9:
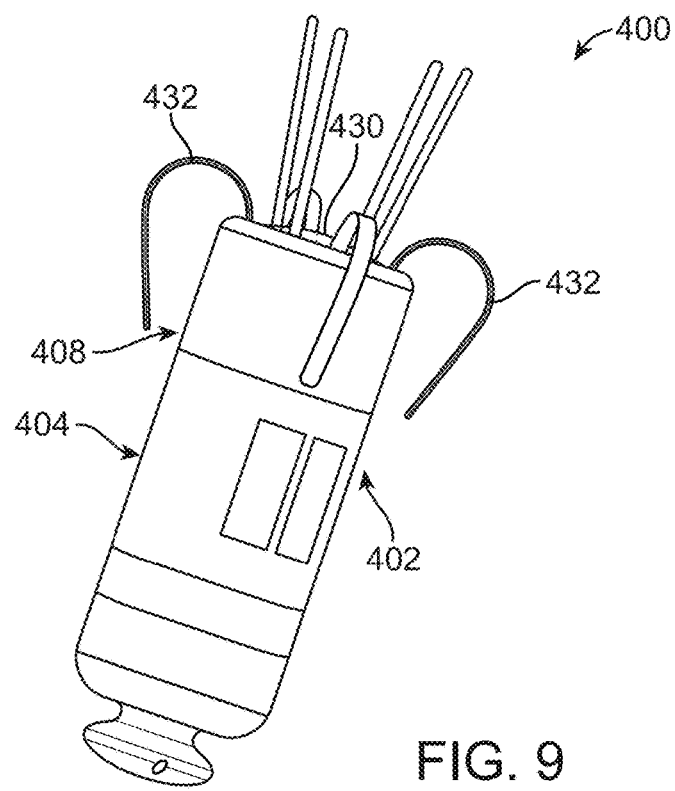
FIG. 9 is a schematic perspective view of another embodiment of an implantable medical device.
Figure 10:
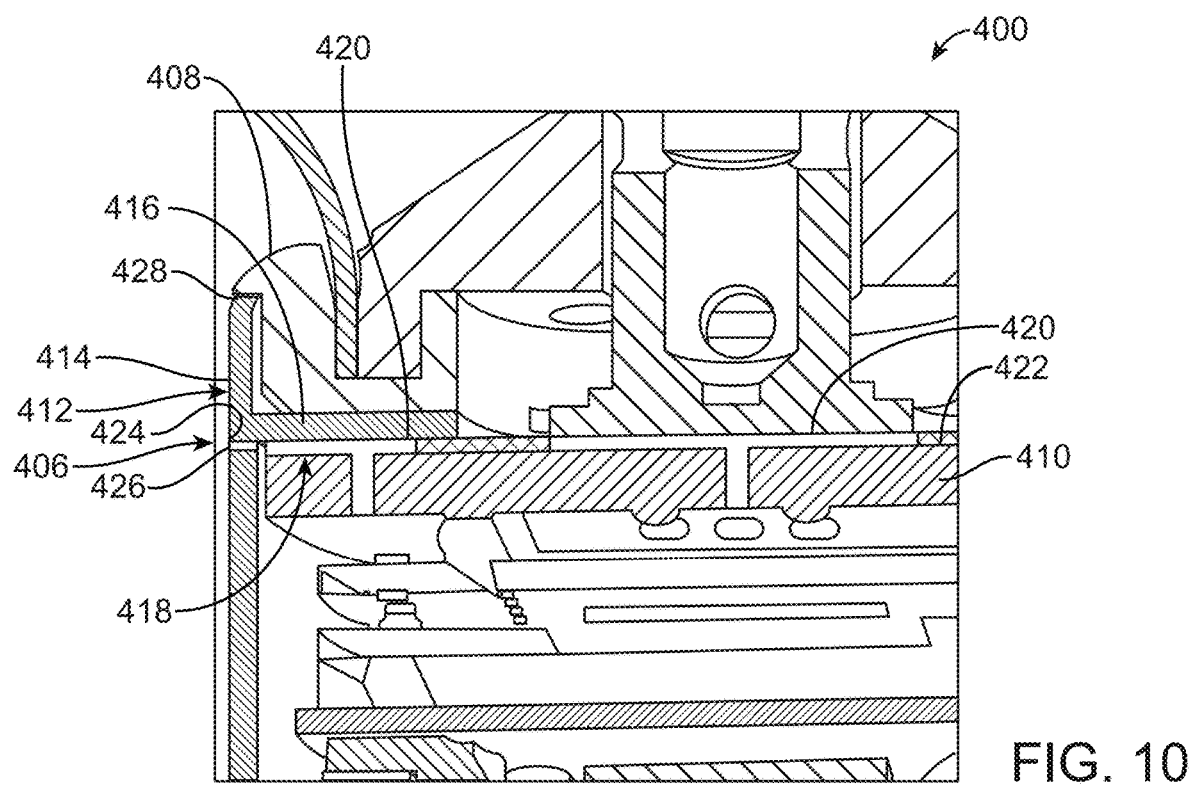
FIG. 10 is a schematic cross-section view of a portion of the implantable medical device of FIG. 9.

As mentioned herein, the various embodiments of feedthrough assemblies described herein can be utilized in any suitable device. For example, FIGS. 9-10 are various views of another embodiment of an implantable medical device 400. All of the design considerations and possibilities regarding the implantable medical device 300 of FIGS. 5-8 apply equally to the implantable medical device 400 of FIGS. 9-10. The device 400 includes a hermetically-sealed package 402 having a housing 404 and a hermetic (e.g., feedthrough) assembly 406 that forms a part of the housing.

The hermetic assembly 406 includes a dielectric substrate 410 and a ferrule 412. The ferrule 412 includes a body 414 and a flange 416 extending from the body. The ferrule 412 is connected to a welding portion 418 of a patterned conductive layer 420 that is disposed between the flange 416 and a first major surface 422 of the dielectric substrate 410 such that the ferrule is hermetically sealed to the dielectric substrate. An edge 424 of the body 414 of the ferrule 412 is connected to an edge 426 of the housing 404.

The hermetically-sealed package 406 also includes a second housing 408 that is connected to a second edge 428 of the body 414 of the ferrule 412. Any suitable technique or techniques can be utilized to connect the second housing 408 to the ferrule 412, e.g., the same techniques described herein regarding connection of the housing 102 and second housing 118 of the hermetically-sealed package 100 of FIG. 3. In one or more embodiments, the second housing 408 includes an external contact 430 that is adapted to provide an electrical signal to tissue of a patient using any suitable technique or techniques. In one or more embodiments, the external contact 430 can be electrically connected to the patterned conductive layer 420 of hermetic assembly 406 using any suitable technique or techniques.

The IMD 400 can take any suitable shape or shapes. In one or more embodiments, at least one of the housing 404, second housing 408, or the dielectric substrate 410 can have an elliptical cross-section in a plane that is substantially parallel to the first major surface 422 of the dielectric substrate 410. Further, the IMD 400 can have any suitable dimensions.

The IMD 400 can further include one or more tines 432 that are connected to the second housing 408 using any suitable technique or techniques. In one or more embodiments, one or more of the tines 432 can be electrically connected to the hermetic assembly 406 using any suitable technique or techniques.

Figure 11:
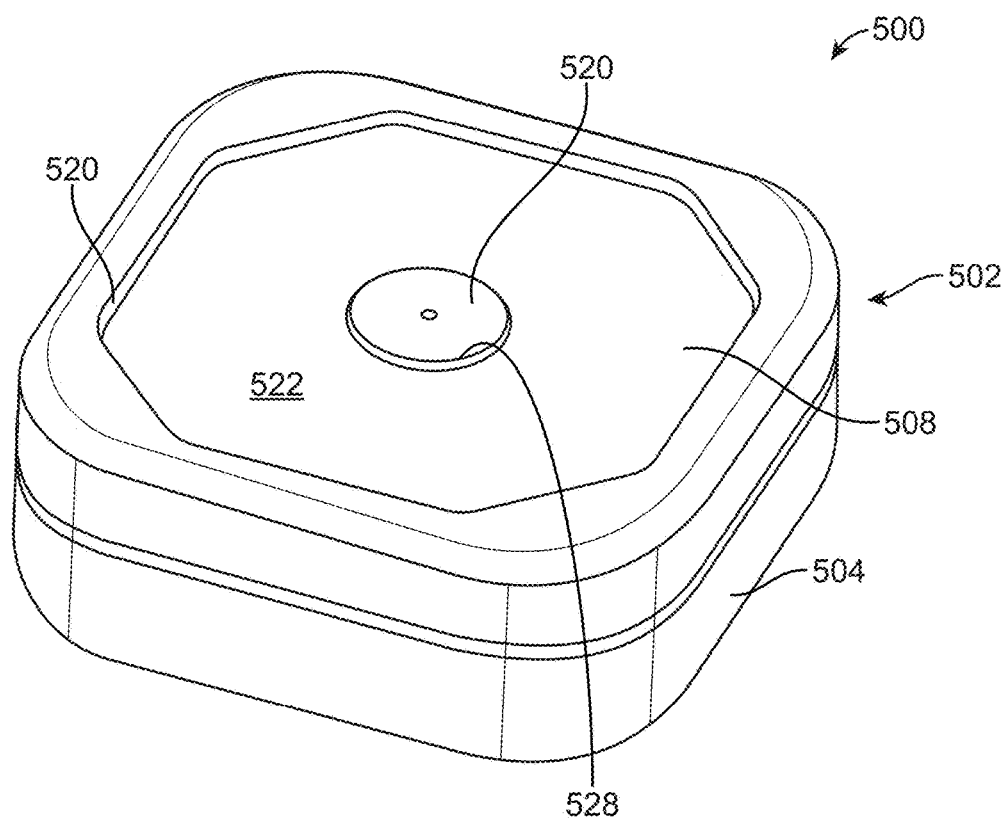
FIG. 11 is a schematic perspective view of another embodiment of an implantable medical device.
Figure 12:
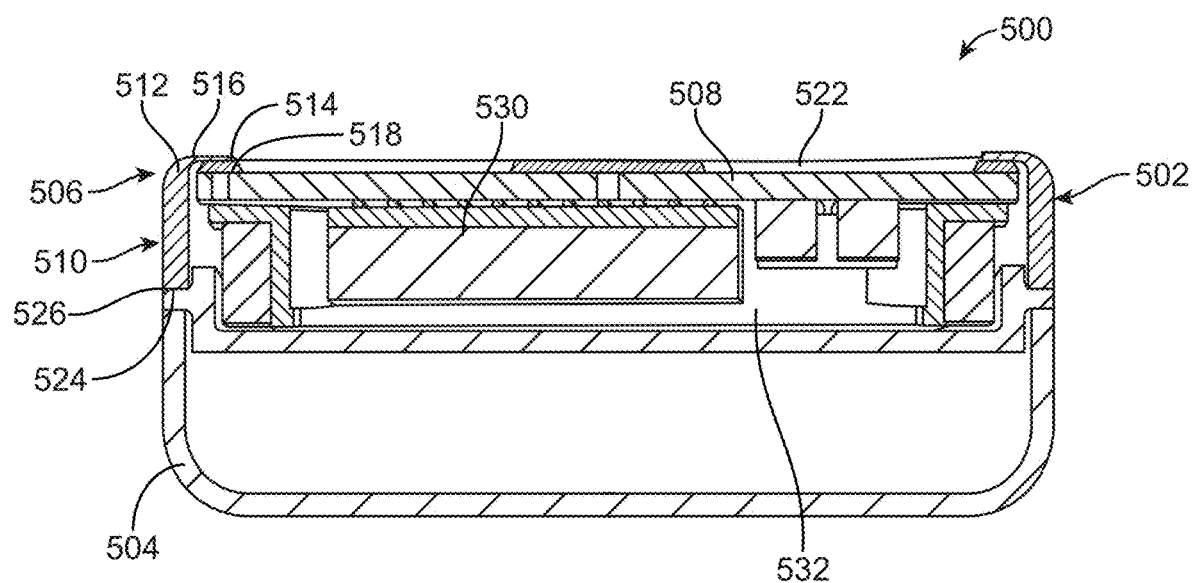
FIG. 12 is a schematic cross-section view of the implantable medical device of FIG. 11.

FIGS. 11-12 are various views of another embodiment of an implantable medical device (IMD) 500. All of the design considerations regarding the implantable medical device 300 of FIGS. 5-8 and the implantable medical device 400 of FIGS. 9-10 apply equally to the implantable medical device 500 of FIGS. 11-12. The device 500 includes a hermetically-sealed package 502 having a housing 504 and a hermetic assembly 506 that forms a part of the housing. Although depicted as including a single hermetic assembly 506, the implantable medical device 500 can include any suitable number of hermetic assemblies.

The hermetic assembly 506 includes a dielectric substrate 508 and a ferrule 510. The ferrule 510 includes a body 512 and a flange 514 extending from the body. As can be seen in FIG. 12, the flange 516 extends from an upper portion 516 of the body 512. The ferrule 510 is connected to a welding portion 518 of a patterned conductive layer 520 that is disposed between the flange 514 and a first major surface 522 of the dielectric substrate 508 such that the ferrule is hermetically sealed to the dielectric substrate. An edge 524 of the body 512 of the ferrule 510 is connected to an edge 526 of the housing 504 using any suitable technique or techniques, e.g., welding.

One difference between the IMD 500 of FIGS. 11-12 and the IMD 400 of FIGS. 9-10 is that the IMD 500 does not include a second housing. Instead, the hermetic assembly 506 forms the upper portion of the sealed package 502 of the IMD 500. Further, the housing 504 connected to the ferrule 510 can be a sealed battery that is electrically connected to the hermetic assembly 506 using any suitable technique or techniques.

In one or more embodiments, the patterned conductive layer 520 can include an external electrode 528 disposed on the first major surface 522 of the dielectric substrate 508 as shown in FIG. 11. The external electrode 528 can be electrically connected to electronic component 530 that is connected to a second major surface 532 of the dielectric substrate 508 using any suitable technique or techniques. In one or more embodiments, the external electrode 528 can be adapted to direct energy (e.g., a signal) to tissue of a patient. In one or more embodiments, the external electrode 528 can be adapted to receive energy from tissue of the patient, thereby functioning as a sensor. In one or more embodiments, the external electric 528 can be adapted to direct and receive energy to and from tissue of a patient.

The IMD 500 can take any suitable shape or shapes. In one or more embodiments, at least one of the housing 504 or the dielectric substrate 508 can take a rectangular shape in a plane that is substantially parallel to the first major surface 522 of the dielectric substrate 508. Further, the IMD 500 can have any suitable dimensions.

As described herein, the various embodiments of hermetic assemblies can be utilized in any suitable application. For example, one or more embodiments of hermetic assemblies can be utilized as an optical window or port that can provide a hermetically-sealed window for viewing of one or more components disposed within a housing connected to the assembly or for emission and detection of electromagnetic radiation that is directed through a dielectric substrate of the assembly. For example, an emitter that is adapted to emit electromagnetic radiation can be disposed within a housing that is in part formed by a hermetic assembly. Such electromagnetic radiation can be directed from within the housing and through a dielectric substrate that is hermetically sealed to a ferrule of the hermetic assembly. Such dielectric substrate, is, therefore, adapted to provide an optical window for the emitter.

Figure 13:
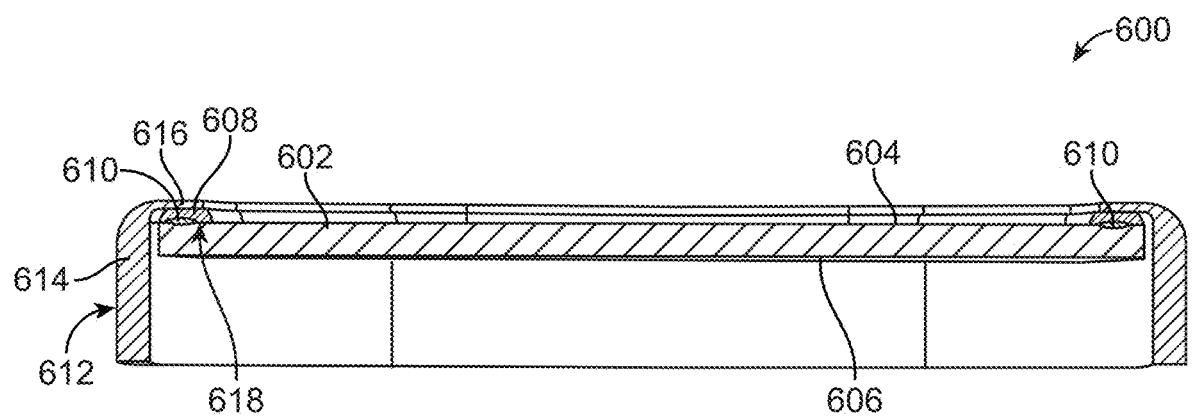
FIG. 13 is a schematic cross-section view of another embodiment of a hermetic assembly.
Figure 14:
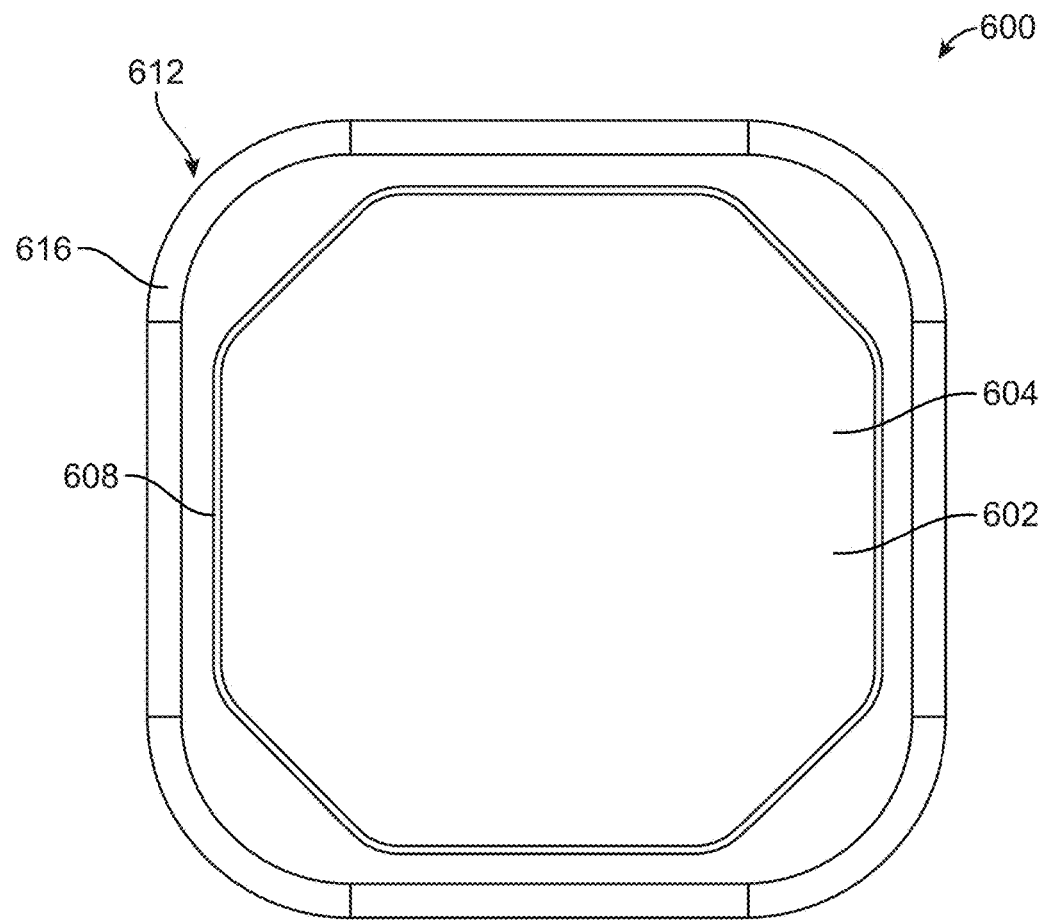
FIG. 14 is a schematic plan view of the hermetic assembly of FIG. 13.

FIGS. 13-14 are various view of one embodiment of a hermetic assembly 600. All of the design considerations and possibilities regarding the hermetic assembly 10 of FIGS. 1-2 and the hermetically-sealed package 100 of FIG. 3 apply equally to the hermetic assembly 600 of FIGS. 13-14.

The hermetic assembly 600 includes a dielectric substrate 602 having a first major surface 604 and a second major surface 606. The assembly 600 further includes a patterned layer 608 connected to the first major surface 604 of the dielectric substrate 602 by a laser bond 610, and a ferrule 612 having a body 614 and a flange 616 extending from the body. The flange 616 is welded to a welding portion 618 of the patterned layer 608 that is disposed between the flange and the first major surface 604 of the dielectric substrate 602 such that the ferrule 612 is hermetically sealed to the dielectric substrate.

The hermetic assembly 600 can be connected to any suitable housing (e.g., housing 102 of package 100 of FIG. 3) using any suitable technique or techniques. Further, the hermetic assembly 600 can be utilized with any suitable system or package, e.g., implantable medical device 500 of FIGS. 11-12.

The various embodiments of hermetically-sealed packages described herein can include any suitable number of hermetic assemblies. For example, FIG. 15 is a schematic cross-section view of another embodiment of a hermetically-sealed package 700. All of the design considerations and possibilities described herein regarding the hermetically-sealed package 100 of FIG. 3 apply equally to hermetically-sealed package 700 of FIG. 15. The package 700 includes a first hermetic assembly 710 and a second hermetic assembly 770. Each of the first and second hermetic assemblies 710, 770 can include any suitable hermetic assembly, e.g., hermetic assembly 10 of FIGS. 1-2. The package 700 can include identical assemblies 710, 770. In one or more embodiments, the first assembly 710 is different from the second assembly 770. Although depicted as including two hermetic assemblies 710, 770, the package 700 can include any suitable number of assemblies.

The assemblies 710, 770 can be connected together using any suitable technique or techniques. In one or more embodiments, a ferrule 722 of the first assembly 710 is connected to a ferrule 772 of the second assembly 770. In the embodiment illustrated in FIG. 15, an edge 758 of a body 726 of the ferrule 722 is connected to an edge 766 of a body 768 of the ferrule 772 by a bond or weld 764. Any suitable technique or techniques can be utilized to form the weld 764, e.g., the same techniques described herein regarding the weld 44 between the flange 26 and the welding portion 28 of the patterned conductive layer 20 of the assembly 10 of FIGS. 1-2.

The hermetic assemblies 710, 770 can form a part of a housing 702 of the package 700. In such embodiments, additional portions of the housing 702 can be connected to one or both of the assemblies 710, 770 to form a hermetically-sealed enclosure 712. In one or more embodiments, the assemblies 710, 770 form the entirety of the housing 702 and provide the hermetically-sealed enclosure 712.

The package 700 can be utilized for any suitable device or system, e.g., an implantable medical device. The package 700 can provide such device sensing of electrical signals within a patient in two distinct directions. Further such device can provide more reliable telemetry with external transceivers as signals can be transmitted through one or both assemblies 710, 770, which may be oriented in different directions. Also, the package 700 can be utilized with an implantable energy transfer system that can be adapted to receive electromagnetic energy through two or more sides of the housing 702 via the assemblies 710, 770.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A hermetic assembly comprising:
a dielectric substrate comprising a first major surface and a second major surface;
a patterned layer connected to the first major surface of the dielectric substrate; and
a ferrule comprising a body and a flange extending from the body, wherein the flange is welded to a welding portion of the patterned layer that is disposed between the flange and the first major surface of the dielectric substrate such that the ferrule is hermetically sealed to the dielectric substrate.

2. The assembly of claim 1, further comprising a feedthrough disposed in the dielectric substrate.

3. The assembly of claim 2, wherein the feedthrough comprises:
a via disposed between the first major surface and the second major surface of the dielectric substrate;
a conductive material disposed in the via; and
an external contact disposed over the via adjacent the first major surface of the dielectric substrate, wherein the external contact is electrically connected to the conductive material disposed in the via.

4. The assembly of claim 3, wherein the external contact of the feedthrough is hermetically sealed to the first major surface of the dielectric substrate by a laser bond that surrounds the via.

5. The assembly of claim 1, wherein the flange further comprises a major surface that contacts the welding portion of the patterned layer.

6. The assembly of claim 5, wherein the major surface of the flange is substantially parallel to the first major surface of the dielectric substrate.

7. The assembly of claim 1, further comprising an electronic component disposed adjacent to at least one of the first major surface or the second major surface of the dielectric substrate, wherein one or more test points are disposed on a surface of the electronic component.

8. The assembly of claim 1, wherein the ferrule further comprises a tab extending from the body and adapted to connect the ferrule to a header.

9. An implantable medical device comprising a hermetically-sealed package, wherein the package comprises:
a housing; and
a hermetic assembly comprising:
a dielectric substrate comprising a first major surface and a second major surface;
a patterned layer connected to the first major surface of the dielectric substrate; and
a ferrule comprising a body and a flange extending from the body, wherein the flange is welded to a welding portion of the patterned layer that is disposed between the flange and the first major surface of the dielectric substrate such that the ferrule is hermetically sealed to the dielectric substrate;
wherein an edge of the body of the ferrule is connected to an edge of the housing.

10. The device of claim 9, wherein the patterned layer is connected to the first major surface of the dielectric substrate by a laser bond.

11. The device of claim 9, wherein the hermetically-sealed package further comprises a second housing connected to a second edge of the body of the ferrule.

12. The device of claim 11, wherein the second housing comprises an external contact adapted to provide an electrical signal to tissue of a patient.

13. The device of claim 11, wherein at least one of the housing, the second housing, or the dielectric substrate comprises an elliptical cross-section in a plane that is substantially parallel to the first major surface of the dielectric substrate.

14. The device of claim 11, further comprising one or more tines that are connected to the second housing.

15. The device of claim 9, wherein the patterned layer comprises an external electrode disposed on the first major surface of the dielectric substrate.

16. The device of claim 15, wherein the external electrode is adapted to at least one of direct energy to tissue of a patient or receive energy from tissue of the patient.

17. The device of claim 15, further comprising an electronic component disposed adjacent to the second major surface of the dielectric substrate, wherein the external contact is electrically connected to the electronic component.

18. A hermetically-sealed package comprising a first hermetic assembly and a second hermetic assembly connected to the first hermetic assembly, wherein each of the first hermetic assembly and second hermetic assembly comprises:
a dielectric substrate comprising a first major surface and a second major surface;
a patterned layer connected to the first major surface of the dielectric substrate; and
a ferrule comprising a body and a flange extending from the body, wherein the flange is welded to a welding portion of the patterned layer that is disposed between the flange and the first major surface of the dielectric substrate such that the ferrule is hermetically sealed to the dielectric substrate.

19. The package of claim 18, wherein the ferrule of the first hermetic assembly is connected to a ferrule of the second hermetic assembly.

20. The package of claim 19, wherein an edge of the body of the ferrule of the first hermetic assembly is connected to an edge of the body of the ferrule of the second hermetic assembly.

* * * * *